(12) United States Patent
Su

(10) Patent No.: US 9,155,466 B2
(45) Date of Patent: *Oct. 13, 2015

(54) EYE IMAGING APPARATUS WITH A WIDE FIELD OF VIEW AND RELATED METHODS

(71) Applicant: Visunex Medical Systems Co. Ltd., Grand Cayman (KY)

(72) Inventor: Wei Su, Sunnyvale, CA (US)

(73) Assignee: Visunex Medical Systems Co. Ltd., Grand Cayman (KY)

(\*) Notice: Subject to any disclaimer, the term of this patent is extended or adjusted under 35 U.S.C. 154(b) by 0 days.

This patent is subject to a terminal disclaimer.

(21) Appl. No.: 14/614,305

(22) Filed: Feb. 4, 2015

(65) Prior Publication Data

US 2015/0146170 A1 May 28, 2015

Related U.S. Application Data

(63) Continuation of application No. 14/191,291, filed on Feb. 26, 2014, which is a continuation-in-part of application No. 13/845,069, filed on Mar. 17, 2013.

(60) Provisional application No. 61/612,306, filed on Mar. 17, 2012.

(51) Int. Cl.
*A61B 3/14* (2006.01)
*A61B 3/125* (2006.01)
*A61B 3/00* (2006.01)

(52) U.S. Cl.
CPC .............. *A61B 3/14* (2013.01); *A61B 3/0008* (2013.01); *A61B 3/125* (2013.01)

(58) Field of Classification Search
CPC ........ A61B 3/125; A61B 3/152; A61B 3/154; A61B 3/156; A61B 3/12; A61B 3/158

USPC ......................................................... 351/244
See application file for complete search history.

(56) References Cited

U.S. PATENT DOCUMENTS 3,944,341 A 3/1976 Pomerantzeff
4,023,189 A 5/1977 Govignon
(Continued)

FOREIGN PATENT DOCUMENTS

JP 2002238853 A 8/2002
WO WO03/057024 A1 7/2003
(Continued)

OTHER PUBLICATIONS

Su et al.; U.S. Appl. No. 14/312,590 entitled "Mechanical Features of an Eye Imaging Apparatus," filed Jun. 23, 2014.
(Continued)

*Primary Examiner* — Jordan Schwartz
(74) *Attorney, Agent, or Firm* — Shay Glenn LLP

(57) ABSTRACT

An eye imaging apparatus can include a housing, an optical imaging system in the housing, and a light source in the housing to illuminate an eye. The optical imaging system can include an optical window at a front end of the housing with a concave front surface for receiving the eye as well as an imaging lens disposed rearward the optical window. The apparatus can comprise a light conditioning element configured to receive light from the light source and direct said light to the eye. The apparatus can further include an image sensor in the housing disposed to receive an image of the eye from the optical imaging system. In various embodiments, light conditioning element includes at least one multi-segment surface. In some embodiments, the housing is provided with at least one hermitic seal, for example, with the optical window. In some embodiments, time sequential illumination is employed.

18 Claims, 12 Drawing Sheets

(56) References Cited

U.S. PATENT DOCUMENTS

| | | |
|---|---|---|
| 4,026,638 A | 5/1977 | Govignon |
| 4,461,551 A | 7/1984 | Blaha |
| 5,046,608 A | 9/1991 | Laipply |
| 5,608,472 A | 3/1997 | Szirth et al. |
| 5,745,212 A | 4/1998 | Volk |
| 5,822,036 A * | 10/1998 | Massie et al. ............... 351/219 |
| 6,267,752 B1 * | 7/2001 | Svetliza ................... 604/294 |
| 6,361,167 B1 | 3/2002 | Su et al. |
| 6,446,795 B1 | 9/2002 | Allen et al. |
| 6,685,317 B2 | 2/2004 | Su et al. |
| 7,048,379 B2 | 5/2006 | Miller et al. |
| 7,357,248 B2 | 4/2008 | Sivakumar et al. |
| 7,445,335 B2 | 11/2008 | Su et al. |
| 7,448,753 B1 | 11/2008 | Chinnock |
| 7,499,634 B2 | 3/2009 | Yogesan et al. |
| 7,621,636 B2 | 11/2009 | Su et al. |
| 7,621,638 B2 | 11/2009 | Su et al. |
| 7,650,064 B2 | 1/2010 | Isogai et al. |
| 7,802,884 B2 | 9/2010 | Feldon et al. |
| 7,815,310 B2 | 10/2010 | Su et al. |
| 7,986,859 B2 | 7/2011 | Fischer |
| 8,002,410 B2 | 8/2011 | Shea |
| 8,118,431 B2 | 2/2012 | Shea et al. |
| 8,328,356 B2 | 12/2012 | Cheng et al. |
| 8,356,900 B2 | 1/2013 | Zhou et al. |
| 8,506,083 B2 | 8/2013 | Zhou et al. |
| 8,518,109 B2 | 8/2013 | Shea et al. |
| 8,777,413 B2 | 7/2014 | Zhou et al. |
| 8,820,929 B2 | 9/2014 | Shea et al. |
| 2002/0097379 A1 | 7/2002 | Goldfain et al. |
| 2003/0174211 A1 | 9/2003 | Imaoka et al. |
| 2004/0118431 A1 | 6/2004 | Flynn |
| 2005/0018135 A1 | 1/2005 | Maeda et al. |
| 2005/0270484 A1 | 12/2005 | Maeda et al. |
| 2006/0176447 A1 | 8/2006 | Reis |
| 2008/0071254 A1 | 3/2008 | Lummis et al. |
| 2008/0211420 A1 | 9/2008 | Walker et al. |
| 2009/0153797 A1 | 6/2009 | Allon et al. |
| 2009/0211586 A1 | 8/2009 | Shea et al. |
| 2010/0091244 A1 | 4/2010 | Volk |
| 2010/0118270 A1 | 5/2010 | Shea et al. |
| 2010/0228236 A1 | 9/2010 | Muhlhoff et al. |
| 2010/0278394 A1 | 11/2010 | Raguin et al. |
| 2011/0085137 A1 | 4/2011 | Kleen et al. |
| 2011/0176109 A1 | 7/2011 | Mann |
| 2011/0299036 A1 | 12/2011 | Goldenholz |
| 2012/0026461 A1 | 2/2012 | Chou et al. |
| 2012/0050683 A1 * | 3/2012 | Yates ........................... 351/219 |
| 2012/0092619 A1 | 4/2012 | Rowe |
| 2012/0099077 A1 | 4/2012 | Abt |
| 2012/0224142 A1 | 9/2012 | Cornsweet et al. |
| 2012/0229617 A1 | 9/2012 | Yates et al. |
| 2012/0249748 A1 | 10/2012 | Nagano |
| 2012/0287255 A1 | 11/2012 | Ignatovich et al. |
| 2013/0057828 A1 | 3/2013 | De Smet |
| 2013/0103014 A1 | 4/2013 | Gooding et al. |
| 2013/0235345 A1 | 9/2013 | Ohban |
| 2013/0301003 A1 | 11/2013 | Wells of al. |
| 2014/0055749 A1 | 2/2014 | Zhou et al. |
| 2014/0063455 A1 | 3/2014 | Zhou et al. |
| 2014/0063456 A1 | 3/2014 | Zhou et al. |
| 2014/0063457 A1 | 3/2014 | Zhou et al. |
| 2014/0063459 A1 | 3/2014 | Zhou et al. |
| 2014/0063462 A1 | 3/2014 | Zhou et al. |
| 2014/0063463 A1 | 3/2014 | Zhou et al. |
| 2014/0078467 A1 | 3/2014 | Su |
| 2014/0085603 A1 | 3/2014 | Su et al. |
| 2014/0125949 A1 | 5/2014 | Shea et al. |
| 2015/0009473 A1 | 1/2015 | Su |
| 2015/0021228 A1 | 1/2015 | Su et al. |

FOREIGN PATENT DOCUMENTS

| | | |
|---|---|---|
| WO | WO2006/013579 A1 | 2/2006 |
| WO | WO2010/096756 A1 | 8/2010 |
| WO | WO2011/022803 A1 | 3/2011 |
| WO | WO2012/118907 A2 | 9/2012 |
| WO | WO2012/154278 A1 | 11/2012 |
| WO | WO2013/020092 A1 | 2/2013 |
| WO | WO2013/162471 A1 | 10/2013 |
| WO | WO2013/165689 A1 | 11/2013 |
| WO | WO2014/074573 A1 | 5/2014 |

OTHER PUBLICATIONS

American Academy of Ophthalmology; Vision Screening for Infants and Children (Policy Statement); American Association for Pediatric Ophthalmology and Strabismus; 3 pgs; © 2013 (earliest approval date: May 1991).

Cho et al.; Development of real-time dual-display handheld and bench-top hybrid-mode SD-OCTs; Sensors (Basel); 14(2); pp. 2171-2181; Jan. 27, 2014.

Device Optical; Kowa Genesis-D Hand Held Retinal Camera (product information); 3 pgs.; retrieved Jun. 23, 2014 from the internet (http://www.deviceoptical.com/pd_kowa_genesisd.cfm).

Haddock et al; Simple, inexpensive technique for high-quality smartphone fundus photography in human and animal eyes; Journal of Ophthalmology; Hindawi Pub. Corp.; vol. 2013; Art. ID 518479; 5 pgs.; 2013 (received Jun. 8, 2013; accepted Aug. 18, 2013).

* cited by examiner

EYE IMAGING APPARATUS WITH A WIDE FIELD OF VIEW AND RELATED METHODS

CROSS REFERENCE TO RELATED APPLICATIONS

This application is a continuation of U.S. application Ser. No. 14/191,291 filed Feb. 26, 2014 which is a continuation-in-part of U.S. application Ser. No. 13/845,069 filed Mar. 17, 2013 which claims the benefit of U.S. Provisional Application No. 61/612,306 filed Mar. 17, 2012, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

STATEMENT AS TO FEDERALLY SPONSORED RESEARCH

None.

BACKGROUND

Various embodiments of the invention relate generally to an eye imaging apparatus and related methods, and for example to an eye imaging apparatus with a wide field of view and related methods.

Eyes are among the most valued human organs that play indispensable roles in life. Likewise, eye diseases and vision loss in general are serious problems. Moreover, eye diseases and vision problems among children, especially new-born babies, can have severe and far-reaching implications. For infants and small children, the visual centers in the brain are not fully mature. For the visual centers in the brain to develop properly, proper input from both eyes is desirable. Therefore good vision can be an important factor in the proper physical development and educational progress.

Undetected eye problems in infants and others may result in irreversible loss of vision. Early detection and diagnosis provide the best opportunity for treatment and prevention of vision loss.

In eye examinations, eye imaging apparatus has become increasingly important. Since retinal and optic nerve problems are among the leading causes in vision loss, eye imaging apparatus capable of imaging a posterior segment of the eye can be particularly useful. Moreover, an eye imaging apparatus with a wide field of view can offer the benefit of enabling evaluation of pathologies located on the periphery of the retina.

SUMMARY OF THE DISCLOSURE

Various embodiments disclosed herein include, although are not limited to, an eye imaging apparatus with a wide field of view, which may be, for example, from 60 degree to 180 degree.

Various embodiments, for example, may comprise an apparatus comprising a housing and a light source disposed inside the housing to illuminate an eye. The apparatus can also include an optical imaging system. The system can include an optical window at a front end of the housing with a concave front surface for receiving the eye. The system can also include an imaging lens disposed rearward the optical window and optically aligned with the optical window along an optical imaging path. The optical imaging system can have an optical axis. The apparatus can comprise a light conditioning element in the housing having at least one multi-segment surface positioned behind the peripheral portion of the optical window. The light conditioning element can be configured to receive light from the light source and direct said light to the eye. The apparatus can include an image sensor in the housing disposed to receive an image of the eye from the optical imaging system.

Various other embodiments comprise an eye imaging apparatus including a housing and an optical window at a front end of the housing. The apparatus can comprise a light conditioning element having at least one multi-segment surface positioned behind the peripheral portion of the optical window. The light conditioning element can be configured to receive light from a light source and direct light to an eye.

In various embodiments, a light conditioning element for an eye imaging apparatus for illuminating an anatomical feature in a medical examination is disclosed. The element can comprise a body having front surface, a back surface, an inner side surface and an outer side surface. The inner side surface and the outer side surface can comprise at least one multi-segment surface. The light conditioning device can be configured to receive light from a light source and direct light to an eye.

Various embodiments disclose an eye imaging apparatus employing sequential illumination. The apparatus can comprise a housing and a light source disposed inside the housing and having a plurality of light emitting elements configured to illuminate different portions of an eye time-sequentially. The apparatus can include an optical imaging system inside the housing. The optical imaging system can comprise an optical window at a front end of the housing. The system can also include an imaging lens positioned behind the optical window and optically aligned with the optical window. An image sensor can be configured to receive a plurality of images of the eye with a same field of view through the optical imaging system while each portion of the eye is illuminated time-sequentially.

In some other embodiments, a compact eye imaging apparatus includes a housing and a light source disposed inside the housing to illuminate an eye. The apparatus can include an optical imaging system. The system can include an optical window with a radius of curvature closely matching a curvature of a cornea of the eye at a front end of the housing. An imaging lens can be optically aligned with the optical window. The imaging lens can be positioned behind and separated from the optical window by a gap. The system can include at least first and second relay lenses. At least one miniature lens with a clear aperture size less than 5 mm can be configured to form the image of the eye based on light received from the at least first and second relay lenses. A miniature image sensor with a format less than 1/1.5" can be configured to receive the image of the eye formed by the at least one miniature lens.

Various other embodiments comprise an eye imaging system comprising an eye imaging apparatus comprising a housing and a light source disposed inside the housing and having a plurality of light emitting elements. The light emitting elements can be configured to illuminate different portions of an eye time-sequentially. The eye imaging system can include an optical imaging system. The optical imaging system can include an optical window at a front end of the housing. An imaging lens can be positioned behind the optical window and optically aligned with the optical window. An image sensor can be configured to receive a plurality of images of the eye with a same field of view through the optical imaging system while each portion of the eye is illuminated time-sequentially. A memory can be configured to temporarily store the plurality of images. A computing and communication unit can be configured to receive and transmit the plurality of images. The eye imaging system can further include an image computing module configured to receive the plurality of images from and exchange data with the eye imaging apparatus. The image computing module can comprise an image processing unit configured to generate a set of instructions to process the plurality of images to create a composite image of the eye.

A method of imaging an eye is also disclosed. The method can include activating a light source to illuminate an eye. An optical window can be contacted with a cornea of the eye. The method can further include conditioning light received from the light source by a light conditioning element having at least one multi-segment surface. The light conditioning device can be configured to receive light from the light source and direct light to the eye. The method can include imaging the eye through an optical imaging system comprising said optical window and an imaging lens. The imaging lens can be positioned behind the optical window and can be optically aligned with the optical window. The method can comprise receiving an image of the eye through the optical imaging system by an image sensor.

A method of imaging an eye configured for sequential illumination is also disclosed. The method can comprise varying an intensity of a plurality of light emitting elements over time to illuminate different portions of an eye. The method can further include imaging the eye through an optical imaging system comprising an optical window and an imaging lens. The optical window can be configured to be in contact with a cornea of the eye. The imaging lens can be positioned behind the optical window and optically aligned with the optical window. The method can include receiving a plurality of images of the eye with a same field of view through the optical imaging system while each portion of the eye is illuminated time-sequentially by an image sensor. The plurality of images can be processed to create a composite image of the eye from the plurality of images.

A stereo eye imaging apparatus is also disclosed. The stereo eye imaging apparatus can include a housing and a light source disposed inside the housing to illuminate an eye. The stereo eye imaging apparatus can also comprise an optical imaging system. The optical imaging system can include an optical window at a front end of the housing with a radius of curvature closely matching a radius of curvature of a cornea of the eye. An imaging lens can be positioned behind the optical window and optically aligned with the optical window. A light conditioning device can be positioned behind the peripheral portion of the optical window that is configured to receive light from the light source and direct light to the eye. A first camera and a second camera can be configured to capture a first image and a second image of the eye through the optical imaging system. Extensions of a first optical axis of the first stereo camera and of a second optical axis of the second stereo camera can be converged onto the eye with a convergent angle.

A hermetically sealed eye imaging apparatus is also disclosed. The hermetically sealed eye imaging apparatus can include a housing with a front end and a light source disposed inside the housing to illuminate an eye. The hermetically sealed eye imaging apparatus can include an optical imaging system. The optical imaging system can include an optical window at the front end with a concave front surface for receiving the eye. The optical imaging system can also include an imaging lens disposed rearward the optical window and optically aligned with the optical window along an optical imaging path. The optical imaging system can have an optical axis. The hermetically sealed eye imaging apparatus can comprise a hermetical seal between the optical window and the front end filled with a hermetically sealing material. An image sensor in the housing can be disposed to receive an image of the eye from the optical imaging system.

In some other embodiments, an eye imaging apparatus comprises a housing with a front end having an inner side surface comprising an alignment edge and a reservoir edge disposed at the front end. The eye imaging apparatus can include a light source disposed inside the housing to illuminate an eye. The eye imaging apparatus can further comprise an optical imaging system. The optical imaging system can include an optical window at the front end with a concave front surface for receiving the eye. The optical imaging system can also comprise an imaging lens disposed rearward the optical window and optically aligned with the optical window along an optical imaging path, the optical imaging system having an optical axis. The optical window can be separated from the alignment edge with a first gap. The optical window can be separated from the reservoir with a second gap larger than the first gap, configured to be a reservoir of a sealing material. An image sensor in the housing can be disposed to receive an image of the eye from the optical imaging system.

Other embodiments also comprise an eye imaging apparatus comprising a housing with a front end comprising an inner side surface comprising an alignment edge and a reservoir edge disposed near the front end. The eye imaging apparatus can include a light source disposed inside the housing to illuminate an eye. The eye imaging apparatus can include an optical imaging system. The optical imaging system can include an optical window at the front end with a concave front surface for receiving the eye. The optical imaging system can comprise an imaging lens disposed rearward the optical window and optically aligned with the optical window along an optical imaging path, said optical imaging system having an optical axis. The optical window can be separated from the alignment edge with a first gap. The optical window can be separated from the reservoir with a second gap larger than the first gap, configured to be a reservoir of a sealing material. A plurality of balls can be disposed between the housing and the optical windows. An image sensor in the housing can be disposed to receive an image of the eye from the optical imaging system.

Various embodiments comprise an eye imaging apparatus comprising a housing with a front end comprising a distal section around an optical window comprising a first material. A proximal section can comprise a second material. The front end can also include a bond, wherein the distal section is connected with the proximal section by the bond. The eye imaging apparatus can include a light source disposed inside the housing to illuminate an eye. The eye imaging apparatus can include an optical imaging system. The optical imaging system can comprise the optical window at the front end with a concave front surface for receiving the eye. The optical imaging system can also include an imaging lens disposed rearward the optical window and optically aligned with the optical window along an optical imaging path, said optical imaging system having an optical axis. An image sensor in the housing can be disposed to receive an image of the eye from the optical imaging system.

Some embodiments of a hermetically sealed eye imaging apparatus with a hermetically sealed removable front imaging module are also disclosed. The hermetically sealed eye imaging apparatus can include a housing and a light source disposed inside the housing to illuminate an eye. The hermetically sealed eye imaging apparatus can include a hermetically sealed removable front imaging module with a front end and a rear end. The hermetically sealed removable front imaging module can include an optical imaging system. The optical imaging system can comprise a first optical window at the front end with a concave front surface for receiving the eye. The optical imaging system can also include an imaging lens disposed rearward the optical window and optically aligned with the optical window along an optical imaging path. The hermetically sealed eye imaging apparatus can include a first hermetical seal between the first optical window and the front end filled with a first hermetically sealing material. The hermetically sealed eye imaging apparatus can include a second optical window at the rear end. The hermetically sealed eye imaging apparatus can include a second hermetical seal between the second optical window and the rear end filled with a second hermetically sealing material. A main module can comprise an image sensor in the housing disposed to receive an image of the eye from the optical imaging system. The hermetically sealed removable front imaging module can be capable of being repeatedly attached to and removed from the main module.

In some embodiments, an eye imaging apparatus comprises a housing with a front end comprising an inner side surface comprising an alignment edge and a reservoir edge disposed at the front end. The eye imaging apparatus can comprise a light source disposed inside the housing to illuminate an eye. The eye imaging apparatus can comprise an optical imaging system. The optical imaging system can include an optical window at the front end with a concave front surface for receiving the eye. The optical imaging system can also include an imaging lens disposed rearward the optical window and optically aligned with the optical window along an optical imaging path, said optical imaging system having an optical axis. The alignment edge can be perpendicular to a side surface of the optical window. The optical window can be separated from the reservoir edge with a gap configured to be a reservoir of a sealing material. An image sensor in the housing can be disposed to receive an image of the eye from the optical imaging system.

In certain embodiments, the eye imaging apparatus comprises a housing, a light source inside the housing, an optical imaging system, a light conditioning element and an image sensor. The optical imaging system includes an optical window configured to be in contact with a cornea of the eye on a forward said of the optical window and an imaging lens positioned rearward of the optical window and optically aligned with the optical window. The light conditioning element comprises a multi-segment surface and is positioned behind the peripheral portion of the optical window and configured to receive light from the light source and direct light to the eye. The image sensor is configured to receive an image of the eye through the optical imaging system.

Various embodiments disclosed herein include an eye imaging apparatus with a wide field of view configured to provide sequential illumination. The eye imaging apparatus comprises a plurality of light emitting elements, an optical imaging system, and an image sensor. The plurality of light emitting elements is configured to illuminate each portion of an eye time-sequentially. The image sensor is configured to receive a plurality of images of the eye with a same wide field of view through the optical imaging system while each portion of the eye is illuminated time-sequentially. In some embodiments, the eye imaging apparatus further comprises an image processing unit. In some embodiments, the eye imaging apparatus may transfer the plurality of images to other computing devices or internet based devices that include an image processing unit. The image processing unit is configured to generate a set of instructions to process the plurality of images to create a single clear image of the eye.

Various embodiments disclosed herein include an eye imaging system with a wide field of view. The eye imaging system comprises an eye imaging apparatus and an image computing module. The eye imaging apparatus comprising a plurality of light emitting elements, an optical imaging system, an image sensor, a memory, and a computing and communication unit. The memory is configured to temporarily store the plurality of images. The computing and communication unit is configured to receive and transmit the image. The imaging computing module is configured to receive the plurality of images from and exchange data with the eye imaging apparatus. The image computing module further includes an image processing unit configured to generate a set of instructions to process the plurality of images to create a single clear image of the eye.

Various embodiments disclosed herein include a method of imaging an eye with a wide field of view. The method comprises activating a light source to illuminate an eye, conditioning the light source using a light conditioning element with a multi-segment surface, and receiving an image of the eye through an optical imaging system by an image sensor. The light conditioning element is configured to receive light from the light source and direct light to the eye.

Various embodiments disclosed herein further include a method of imaging an eye by sequential illumination. The method comprises activating a plurality of light emitting elements time-sequentially to illuminate different portions of an eye at different times, imaging the eye through an optical imaging system, and receiving a plurality of images of the eye with a same wide field of view through the optical imaging system while each portion of the eye is illuminated time-sequentially by an image sensor, and processing the plurality of images to create a single image of the eye.

Some embodiments disclosed herein include an eye imaging apparatus configured to generate a three-dimensional image. The three-dimensional eye imaging apparatus comprises a light source, an optical imaging system, a light conditioning element, a first image sensor and a second image sensor configured to receive a first image and a second image of the eye. A first optical axis at the first image sensor and a second optical axis at the second image sensor extend to and converge onto the eye at an angle (e.g., convergent angle) with respect to each other.

Various embodiments disclosed herein include a compact eye imaging apparatus with a wide field of view. The eye imaging apparatus comprises a light source inside a housing, an optical imaging system, and a miniature image sensor. The optical imaging system includes an optical window, an imaging lens, two sets of relay lenses and a set of miniature lenses. The format for the camera comprising the miniature lens or lenses and the sensor is less than 1/2.2 inches or 1/3.2 inches in some embodiments with as sensor size between less than 8.0×6.0 mm or 7.0×5.0 mm and an camera size of less than 10 mm×10 mm or 9 mm×9 mm.

Various embodiments disclosed herein include a hermetically sealed eye imaging apparatus. The housing of the hermetically sealed eye imaging apparatus surrounds and fits with an edge of an optical window. The imaging lens is positioned rearward of the optical window and separated from the optical window by a small gap. The optical window is separated from a first portion of the housing by a first gap, which is configured to align the optical window. The optical window is also separated from a second portion of the housing by a second gap, which is configured to be a reservoir of a hermetically sealing material. A hermetical seal is disposed between the optical window and the housing. The hermetic seal is airtight and watertight and can withstand remain intact with exposure to the high temperatures of an autoclave that is used for sterilization.

Various embodiments disclosed herein include a hermetically sealed eye imaging apparatus with a hermetically sealed removable front imaging module. An optical window and imaging lens are positioned within the hermetically sealed removable front imaging module. An image sensor is positioned within the main module. A first hermetical seal is disposed between the optical window and a housing for the front imaging module, and a second hermetical seal between the housing and a second optical window, which is exposed from a rear portion of the hermetically sealed removable front imaging module. The hermetically sealed removable front imaging module is capable of being removed from the main module.

Various embodiments disclosed herein include an eye imaging apparatus with a wide field of view of 120 degrees or lager. The eye imaging apparatus is capable of imaging the posterior segment of the eye, and, in various embodiments, obtains high quality images with high contrast. In various embodiments, the images of the posterior segment of the eye acquired by the eye imaging apparatus are essentially glare free or haze free, or have negligible glare or haze, even for the patients with dark pigmentation in the eyes.

Various embodiments comprise an eye imaging apparatus that is compact and configured to be hand-held. Various embodiments are sufficiently compact so as to be carried by in a carrying case, e.g., a small carrying case with a handle, or in other convenient manners due to its compactness. Various embodiments may be easily operated by the operators with the little training. Various embodiments meet the needs of patients who do not have convenient access to hospitals or eye care facilities. The eye imaging apparatus provides more opportunities for treatment and prevention of vision loss. In particular, eye imaging apparatus described herein potentially has far-reaching significance for the physical development and educational progress of small children in rural areas.

Furthermore, various embodiments of hermetically sealed eye imaging apparatus are capable of withstanding the sterilization procedure in an autoclave, thus reducing or eliminating the possibility of cross-contamination among patients. Various embodiments of the hermetically sealed eye imaging apparatus are suitable to be used in surgical applications.

DETAILED DESCRIPTION

The present invention now will be described in detail with reference to the accompanying figures. This invention may be embodied in many different forms and should not be construed as limited to the exemplary embodiments discussed herein.

Various embodiments of the present disclosure describe an eye imaging apparatus. In some embodiments, this eye imaging apparatus has a wide field of view. The field of view, may in certain embodiments be at least 60 degree and up to 180 degree. In some embodiments, the field of view is at least 120 degrees but no more than 180 degrees. Various embodiments of the eye imaging apparatus may, for example, comprise a housing, a light source inside the housing to illuminate an eye, and an optical imaging system inside the housing. The optical imaging system may include an optical window configured to be in contact with a cornea of the eye forward the optical window, an imaging lens positioned behind the optical window and optically aligned with the optical window, a light conditioning element having a multi-segment (e.g., reflective and/or refractive) surface configured to receive light from the light source and direct light to the eye, and an image sensor configured to receive light from the eye through the optical imaging system. In some embodiments, the light conditioning element is positioned behind a peripheral portion of the optical window. Also, in some embodiments, the imaging apparatus may further comprises a memory configured to temporarily store images, and a computing and communication subsystem including a touch screen monitor configured to receive, display and transmit the image.

Figures 1A, 1B:
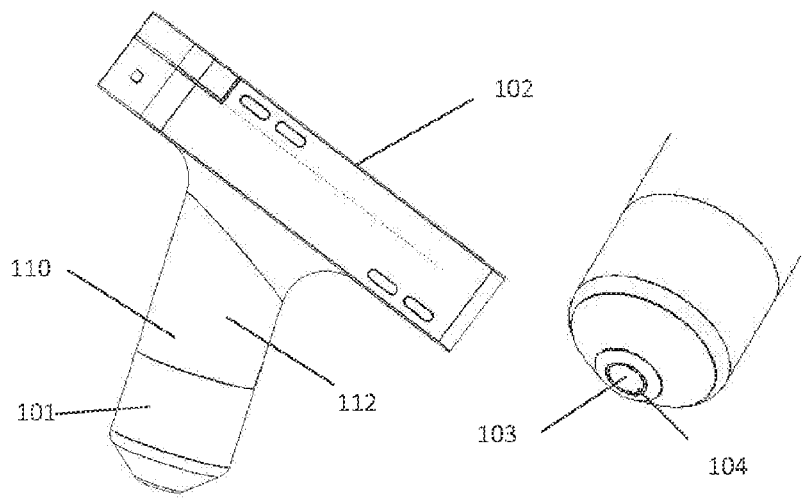
FIG. 1(A) schematically illustrates a side view of an eye imaging apparatus according to one embodiment of the present invention.
FIG. 1(B) schematically illustrates the bottom view of an eye imaging apparatus according to one embodiment of the present invention.

FIG. 1(A) and FIG. 1(B) schematically illustrate a side view and a bottom view of an eye imaging apparatus according to various embodiments of the present invention. The eye imaging apparatus may be compact and in various embodiments has a size less than 250 mm along the longest dimension thereof. For example, in some embodiments the eye imaging apparatus may be between 250 mm and 200 mm, 150 mm, or 100 mm along the longest dimension. In some embodiments, the eye imaging apparatus may weigh less than 1 kg. For example, the eye imaging apparatus may weigh between 1 kg and 0.5 kg, or 0.3 kg, or 0.2 kg in some embodiments. The eye imaging apparatus may be carried by the users in a small carrying case with a handle, for example, that is less than 600 mm×400 mm×300 mm and weigh less than 15 kg or in another convenient manner due to its compactness. In some embodiments, for example, the carrying case is between (600 mm and 300 mm)×(400 mm and 200 mm)×(300 and 150 mm). Also, the carrying case weighs between 15 kg and 10 kg or 5 kg, in some embodiments. Sizes outside these ranges for the eye imaging system and the carrying case are also possible. Various embodiments may be easily operated by the operators with little training.

The imaging apparatus may have a portion constructed to be in a cylindrical shape to allow easy grabbing by one hand and usable as a handle with a display and/or user input interface such as a touch screen monitor 102 mounted at the top of cylindrical part 101. The users may precisely adjust the position/angle of the apparatus with one hand freeing another hand to work on other tasks, for example, opening the eyelids of the patient with the fingers.

Captured images may be transferred to other computing devices or interne based devices, like storage units, through wired or wireless communication systems. In some embodiments, the imaging apparatus is powered by a battery. Also in various embodiments, live images may be displayed on the touch screen monitor or a larger display monitor that receives data from this imaging apparatus in real time. The eye imaging apparatus may be used as a diseases screening or medical diagnosis device for the ophthalmic applications. It may be used in remote rural areas where traveling to the eye care facilities is not convenient. It may also be used as a portable medical imaging device for other medical needs such as ENT or dermatology. Furthermore, the imaging apparatus may have applications in areas other than medical applications, for example, for security screening applications where the images from the posterior/anterior segment of the eye may be used for the personal identification purpose.

The eye imaging apparatus may also be used to image the eyes of animals. For example, the eye imaging apparatus may be used, with or without modification of optics from its human use, to image or photograph the eyes of animals such as livestock, pets, and laboratory test animals, including horses, cats, dogs, rabbits, rats, guinea pigs, mice, etc.

The eye imaging apparatus may comprise a front imaging module and a main module. The eye imaging apparatus may be built as one piece or two separate pieces, as shown as 101 and 112, in the FIG. 1(A) and FIG. 1(B). In some embodiments, the front imaging module 101 may be removed or replaced with other functioning modules which may contain different optics. For example, front imaging modules with higher magnification, front imaging modules designed for premature babies, front imaging modules designed for adult, front imaging modules designed for fluorescein angiography imaging, front imaging modules for NIR imaging and front imaging modules for anterior segment imaging can be used in different circumstances. Accordingly, in designs where the front imaging module is replaceable or removable, the eye imaging apparatus's potential use or applications may be significantly expanded. An optical window is exposed on the outside of the housing of the imaging apparatus enabling light to enter into and exit out of the housing. In various embodiments, the eye can be place proximal to or up against the optical window to obtained images of the eye. The window has central and peripheral portions 103, 104. The central portion 103 of the window is employed as the entrance into the housing for light reflected from the eye that is used to image the eye. The peripheral region 104 of the window, which is disposed about the center 103, is configured for egress of light from the housing such as for example projecting light onto and/or into the eye to illuminate the eye.

In some embodiments, the imaging apparatus may be used to acquire images of the posterior segment of the eye with various magnifications and under the illumination from broadband or narrow spectral light sources. The spectrum of the light source may be in the visible, IR, near IR, UV light range or combinations thereof. To obtain a wide field of the view (FOV), the optical window may be placed over the cornea of the eye with slight pressure. Accordingly, the optical window may have a concave surface matching the size of the cornea, In some embodiments, for example, the outer surface of the optical window has a radius of curvature of between 6 mm and 15 mm. An optical transparent index matching gel with sufficient viscosity may be placed between the cornea and the optical window. The viscosity of the index matching gel may be at least 100 centipoise, 200 centipoise or 300 centipoise. The iris of the patient may or may not be dilated with special drugs. In some embodiments, the imaging apparatus may also be used to obtain images of the anterior segment of the eye by using a front imaging module designed for imaging the anterior segment, using the same illumination system.

Figure 2:
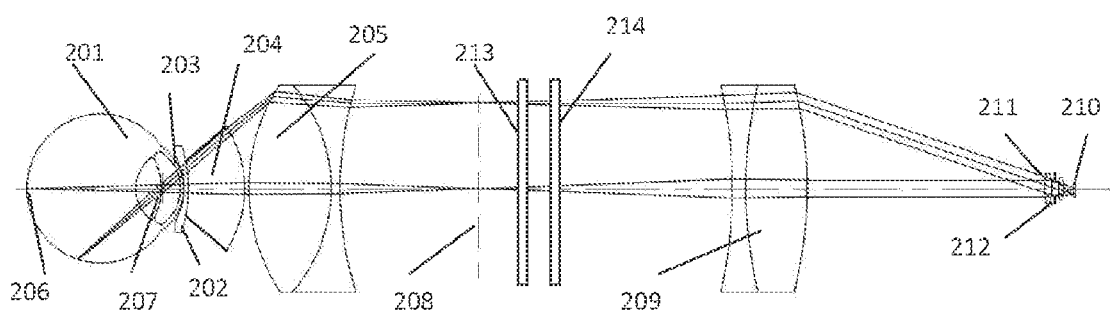
FIG. 2 schematically illustrates one embodiment of the optical design of the eye imaging apparatus showing illumination and imaging optical systems.

FIG. 2 schematically illustrates one embodiment of the optical design or optical system of the eye imaging apparatus, where the posterior segment of the eye 201 is imaged or photographed by the eye imaging apparatus. The optical imaging system of the eye imaging apparatus includes an optical window 203 and an imaging lens 204. The optical window 202 is configured to be in contact with the cornea 203 and may have a concave surface that matched the curvature of the eye. In various embodiments, for example, the radius curvature of the outer surface of the optical window 202 is between about 6 mm and 15 mm. The imaging lens 204, which may include one or multiple lens elements, is positioned behind the optical window 202, on the opposite side of the window as the eye, and optically aligned with the optical window 202. The optical axis of the window and imaging lens may, for example, be substantially aligned with the optical axis of the eye in some cases but not all. For example, the practitioner may examine the eye in a manner that the optical axis of the imaging system is substantially aligned with the optical axis of the eye, however, in some cases, the practitioner tilts the eye imaging apparatus such that these axes are not aligned. Although the radius of the curvature for the frontal optical surface of the optical window 202 is chosen to closely match that of the cornea, the back surface of the optical window may be flattened out slightly depending on the design of the optical illumination system. The optical window 202 may be made from the same or different optical materials as the imaging lens 204. For a wide field of view optical imaging system, the use of the optical index matching gel between the optical window 202 and cornea 203 helps to eliminate significant amount of optical aberrations originated from the cornea of the eye. The curvature of the frontal surface of the imaging lens 204 may be the same as that of the back surface of the optical window 202, or different. The back surface of the imaging lens 204 may be either spherical or non-spherical to obtain desired result for the images. In some embodiments, a small gap of air or other material is placed between the optical window 202 and the imaging lens 204, although the two optical components may be in contact in certain areas or even bonded or affixed together with adhesive.

In some embodiments, the optical imaging system may further includes a first set of relay lenses 205 configured to form a secondary image 208 of the eye near a back focal plane of the first set of relay lenses, a second set of relay lenses 209 configured to project the secondary image 208 to infinity with a front focal plane positioned near the back focal plane of the first set of relay lenses. In various embodiments, a set of miniature lenses 211 is positioned near the back focal plane of the second set of relay lenses and configured to deliver light from the eye to the image sensor 210. A miniature camera comprising the miniature lens or lenses and the sensor has a format no more than 1/2.2 inches or 1/3.2 inches with a focal length of about 4 mm or less, for example between about 4 mm and 2 mm or 4 mm and 3 mm, etc. The view angle for the miniature lens or lenses may be 75° or less with a sensor appropriately sized based, for example, on the focal length of the miniature lens. The camera module, which includes the sensor chip and the miniature lens or lenses is about 8.5×8.5 mm, or between 10 mm×10 mm and 5 mm×5 mm or smaller, for example. In some embodiment, for example, the set of miniature lenses 211 have aperture sizes between about 0.8 mm and 1.5 mm while the first and second relay lenses 205, 209 have aperture sizes of about 20 mm, for example between about 30 mm and 10 mm or 25 mm and 15 mm in some embodiments. The optical imaging system may gather light reflected from the posterior segment or more specifically the retina of the eye 206. The light passes through the center of the iris opening and the crystalline lens of the eye 207, and forms a real image (of the posterior segment or retina) at the secondary image plane 208. As discussed above, the imaging lens 204 may include single or multiple lenses, with spherical or non-spherical surfaces. In some embodiments, the secondary image plane 208 is located near the back focal plane of lens 205. In some embodiments, a relay lens 209 may be used to project the image from the secondary image plane 208 to infinity when the front focal plane of the lens 209 is also placed near the secondary image plane 208. A miniature image sensor 210, either in form of CCD, CMOS or other types, with its own miniature lenses 211, may be positioned near the back focal plane of the lens 209 along the optical axis of the optical imaging system. The miniature lenses 211 may include multiple optical lenses. In some embodiments, the image sensor 210 has an active area that is about 6.2 mm×4.6 mm or, for example, between about 8 mm and 4 mm×6 mm and 3 mm or between about 7 mm and 5 mm×5 mm and 4 mm. Accordingly, in various embodiments the active areas of the sensor 210 are about ¼ of the aperture size of the relay lenses 205, 208 or for example between about 0.4 and 0.2 or 0.5 and 0.1 the size thereof. The diagonal of the sensor 210 are also about 1.4 times of focal length of the miniature lenses 211 or, for example, between about 1.6 and 0.8 times of the focal length.

In some embodiments, the optical imaging system has an aperture 212 that is disposed in the set of miniature lenses 211. FIG. 2, for example, shows the aperture 212 positioned between lenses comprising the set of miniature lenses 211 and in front of the miniature image sensor 210. In some embodiments, the aperture 212 of the optical imaging system is positioned in front of the set of miniature lenses 211. In some such embodiments the aperture 212 is disposed between the miniature lenses 211 and the relay lens 209, however, possibly closer to the miniature lenses. Because the designed object plane for the miniature lenses 211 is at infinity, the use of such miniature lenses may bring the retinal image from the infinity to the image sensor 210. In various embodiments, the miniature lenses 211 are built with a circular optical aperture (iris) 212, which may be located between miniature lenses in the set of miniature lenses or formed by an aperture plate in front of the miniature lenses 211. In certain embodiments such location of the iris 212 reduces optical aberration. The miniature lenses 211 may not only relay the image of the retina 206 to the image sensor 210, but also form an entrance pupil for the optical imaging system near the surface of crystalline lens 207 when the aperture 212 becomes the aperture of the entire optical imaging system. This special arrangement helps to eliminate significant amount of scattering light from the anterior chamber of the eye and the optical elements in the optical imaging system.

In various embodiments, one or more of the miniature lenses in the lens group 211 are configured to be moved or adjusted, for example, longitudinally along the optical axis of the optical imaging system with respect to one or more other of the miniature lenses in the lens group 211, to change the effective optical focal length of the set of miniature lenses, which changes in magnification and results in an optical zoom for the images acquired. Additionally, or alternatively, miniature lenses in the lens group 211 are configured to be moved or adjusted, for example, longitudinally along the optical axis of the optical imaging system to adjust the position of the entire miniature lens group 211 to change the effective focal length of the optical imaging system. In various embodiments, therefore the effective focal length of the whole imaging system is changed while the focal length of the miniature lens group is unchanged thereby providing adjusting the focus of the imaging system. Actuators such as voice coils, piezos, stepper motors or other types of actuators or combinations thereof may be used to longitudinally translate one or more or all of the miniature lenses to change the effective focal length(s) and/or provide zoom. In various embodiments, focusing adjustment of the retinal image on the image sensor 210 may be similarly provided by a built-in focusing mechanism that moves one or more of the miniature lenses 211. Again, an actuator that translates one or more of the miniature lenses in a longitudinal direction along the optical axis may be employed. An auto-focus capability for the imaging apparatus may be realized through the same mechanism in the miniature lenses 211 when a closed loop control mechanism is implemented. In various embodiments, for example, a voice coil or other electrically controlled actuator may be employed and controlled electronically. In various embodiments, the focusing status of the retinal image on the image sensor 210 is determined by comparing the sharpness of the image for multiple lens positions in real time. The size of the retinal image may also be changed through the optical zooming function of the miniature lenses 211 when the effective focal length of the miniature lens group is adjustable. In various such embodiments, electronics may be used to drive the actuator and control the focus and/or zoom. Signals from the electronics to the actuator for varying the focus and/or zoom may be based on input from a user and/or evaluation of the image such as image quality. In certain embodiments, the shape or index of refraction of the lens or lenses in the miniature lens group can be altered in addition to or alternative to changing adjusting the position for altering magnification, zoom, and/or focus. Control electronics may drive such change in shape or refractive index.

In some embodiments, a second optical window 213 may be installed when the imaging system is built into two separated modules: the front imaging module and the main module. The optical window 213 and the imaging lens 204 are positioned within the removable front imaging module. The image sensor 210 is positioned within the main module. The front imaging module is capable of being removed from the main module. The second optical window 213 may be exposed from a rear portion of the removable front imaging module. It may seal off the optics from the environment outside, especially to prevent dust from depositing onto the surface of relay lens 205 which may be visible in the images. Such a window 213 may also seal off the moisture during the sterilization procedure if the removable front imaging module is in an autoclave. Similarly, a third optical window 214 may also be installed on the main module to seal off the rest of the optics from dust. The third optical window 214 may be exposed from a front portion of the main module. The imaging apparatus therefore may be divided into two pieces which, in various embodiments, join at location at or between the two optical windows 213 and 214.

FIG. 2, as do other drawings, show example optical designs. Accordingly, the number of lens element or optical components, for example, in each lens as well as their shapes, locations, configurations, and arrangement may vary. For example, although the first relay lens 205 is shown in FIG. 2 as a cemented doublet and with one concave and one convex outer surface, this relay lens may comprise a group of lenses including one cemented doublet and one air spaced singlet. In various embodiments, however, one or more optical elements are included that provide the function of a relay lens such as the relay lens 205.

Figure 3:
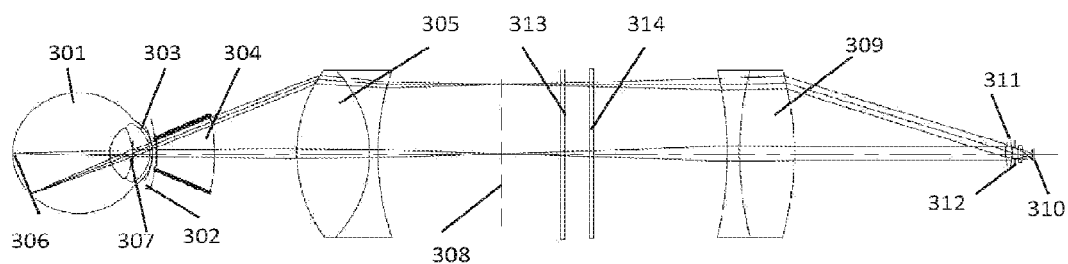
FIG. 3 schematically illustrates another embodiment of the optical design of the eye imaging apparatus showing the illumination and imaging optical systems.

Another embodiment of the optical design is schematically illustrated in FIG. 3. The optical imaging system in this alternative embodiment, comprising an optical window 302, imaging lens 304, and relay lens 305, works in similar manner as the one shown in FIG. 2, but generates images with a smaller field of view as shown in FIG. 3. The front part of the imaging apparatus is different than that shown in FIG. 2, while the rest of imaging system is the same as that shown in FIG. 2. Accordingly, the components shown in FIG. 2 as 209, 210, 211, 212, 213 and 214 are same as the components shown in FIG. 3 as 309, 310, 311, 312, 313, and 314 respectively. In some other embodiments, different optical imaging systems with special features or designs may be used that have different performance characteristics and/or allow the imaging apparatus to be used on different eyes or even subjects, for example, adult eyes, horse eyes, dog or cat eyes, and rabbit eyes etc.

Figure 4:
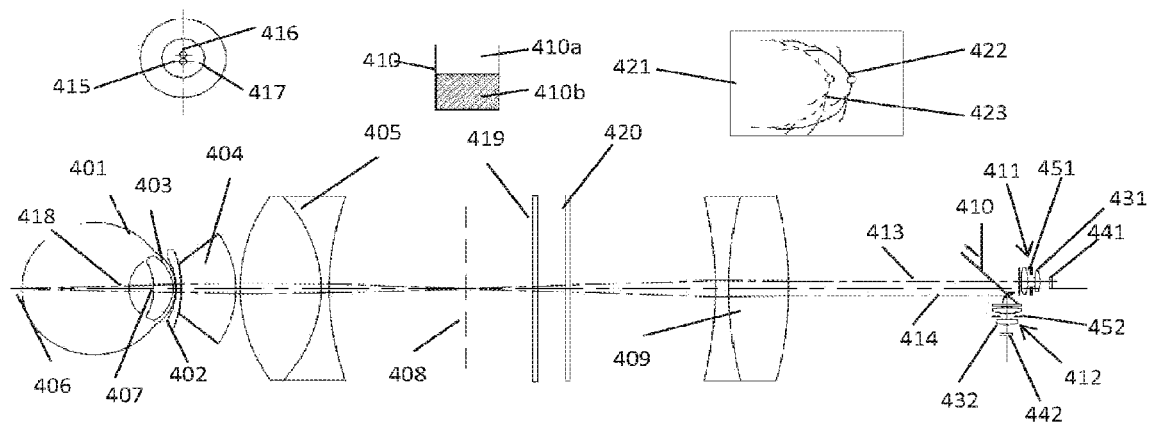
FIG. 4 schematically illustrates one embodiment of a three-dimensional eye image apparatus.

FIG. 4 schematically illustrates one embodiment of a three-dimensional eye image apparatus. The retina 406 may be imaged or photographed when the contact optical window 402 is placed against the cornea 403 of the eye 401. After the light from the retina is passed through the center of the crystalline lens 407 in the eye, a real image of the retina is formed at the secondary image plane 408 by the imaging lens 404 and first relay lens 405. The front focal plane of the second relay lens 409 is disposed near the secondary image plane 408. Two imaging modules 411 and 412, each includes miniature lenses 431 and 432 and an image sensor 441 and 442 similar to that in FIG. 2, are placed near the back focal planes of the second relay lens 409 (one of the focal planes being folded by a beam splitter 410). The beam splitting device 410 is used to provide two separate optical paths for the imaging modules 411 and 412, for respective, left and right channel. In various embodiments, the modules 411 and 412 having optical axes 413, 414 are directed toward the eye by the beamsplitter 410 such that the optic axes are parallel but spaced apart by a fixed distance between the second relay lens 409 and the beamsplitter 410. These axes 413 and 414 converge on the eye, e.g., the retina and/or posterior segment and thus are angled inward and convergent at the optical window 402 and/or entrance pupil of the imaging system. Individual optical apertures 451, 452 in the respective imaging modules 411, 412 are relayed backward by the optical lenses in the respective optical paths from the apertures to the eye and thereby form two entrance pupils near the crystalline lens 407. The inset in FIG. 4 shows a side view of the dual entrance pupils 415, 416 which are located near the center of the iris opening 417 of the eye, and are the images of optical apertures 451 and 452 respectively.

In some embodiments, the extension of the optical axes of 413, 414 are not parallel but eventually converged on to the retina 406 in the eye, and result in a small convergent angle 418 therebetween on the forward side of the imaging lens 404 and optical window 402. The amount of separation between the optical axes 413, 414 at the imaging modules determines the convergent angle 418. The convergent angle 418 determines the stereoscopic effect of the 3D images recorded. In various embodiments, after the imaging system is correctly calibrated, the focusing status of the retinal images may be adjusted by superimposing the two images 422 and 423 that are formed on and recorded by the two image sensors 441 and 442. For example, as seen in the screen frame 421, in various embodiments, if the features in the center of two images 422 and 423 are not fully overlapped, the images are out of focus. Using software to detect the disparity of two images and a close-loop control mechanism, the best focus of the retinal images may be achieved quickly and precisely by providing that the two images are at least substantially or in some embodiments completely overlap to each other. As discussed above, actuators may be employed to adjust the focus by varying the longitudinal position of one or more lenses such as one or more miniature lens and/or of the optical sensor in one or both of the imaging modules 411, 412. The movement of the actuator may be driven by electronics controlled by one or more feedback signals that assesses the image data obtained. As discussed above, in various embodiments the actuator may comprise a voice coil. Evaluation of the relative positions of the same features in two images, for example, whether the artery/vein in the left image is located at either left or right side of same artery/vein in the right image, may be used to determine the direction of the focus adjustment. The position of each image sensor is pre-calibrated so that the individual image is in focus when two images are fully overlapped. When the captured stereoscopic images are displayed in a 3D screen, users may see the depth of the objects in the posterior segment of the eye clearly. Accordingly, various embodiments include a 3D display. Similar to the embodiments discussed before, optical windows 419, 420 may be included in the respective front imaging module and main module at the junction therebetween to prevent dust and to build the imaging apparatus autoclave ready.

Different approaches can be used to split the beam and thus the beam splitting device 410 may comprise different types of optical elements and/or arrangements. In some embodiments, the device 410 may comprise a total reflective mirror configured to be inserted into place and removed therefrom or folded down and back up at a rapid rate. At the position shown in FIG. 4, the light from eye is guided to the imaging module 412. After one or more images is taken by module 412, the device 410 may be either pulled up or out of its previous position to allow the light from the relay lens 409 to enter the imaging module 411. As a result, two images are recoded sequentially and at a rapid rate by two image sensors when the various actions are synchronized. In some embodiments, the device 410 may comprise and be split into a transparent section 410a and a reflective section 410b that are laterally disposed with respect to each other. In various such embodiments, a dividing line between the transparent and reflective sections 410a, 410b may be aligned with the center of the optical axis of the imaging system. The light from the eye, before reaching the module 411, may pass through the transparent section 410a of device 410, while the light to module 412 may be reflected by the reflective section 410b. Here, the shutters (if any) of both image sensors may be synchronized to take images simultaneously. In other embodiments, the two imaging modules 411, 412 may be arranged to be side-by-side and with their optical axes in parallel with an appropriate separation of the two optical apertures to provide the stereo or 3D effect. Although the optical axes of the imaging module 411, 412 may be arranged in parallel, a small convergent angle may be provided at the retina. Accordingly, these optical axes may be angled inward and convergent at the optical window 402 and/or entrance pupil of the imaging system. The optical power of the first relay lens 405 may contribute most of such convergence of these optical axes at the optical window, entrance pupil, and eye (e.g., retina). In various embodiments the convergence angle is about 6.5.degree. or less and may for example range from 8.degree. or 7.degree. to 3.degree., 4.degree., or 5.degree. or any combination thereof as well as outside such ranges. In some embodiments, a fixed but partially transmissive, partially reflective beamsplitter 410 can be employed to split the imaging light for directing to the respective imaging modules 411 and 412.

In some embodiments, the use of a stereoscopic imaging arrangement may also allow implementation of more sophisticated techniques to improve the image quality of retinal images. In various embodiments, for example, software is used to analyze the separation of the suspected artifacts in two stereoscopic images. This measured separation can be compared with the separation of the observed features on the retina. The difference in the separation is directly related to the distance of the object in the vitreous to the retina. If this difference in the separation is larger than certain criteria, then the artifacts that may be removed from the images, are present.

The separation of the features (artifacts) shown on images from the first and second stereo cameras is related to the distance from the object that produced such image features to the retina, which in this case is the convergent point of the stereo cameras. The farther away from the retina, the larger the separation (in horizontal direction, or the along the axis separating two cameras). In other words, if the object is located exactly at the convergent plane, e.g., the retina, the two image features are located at exactly same place when two images from the first and second stereo cameras are superimposed to on each other. Using a suitable image process technique, such as image convolution, reference point tracking or other approaches, common features in images captured at the same time by the first and second stereos cameras that manifest a separation when the images are superimposed can be identified and the separation can be measured. If the objects are determined to be far away from the plane where the axes of the first and second stereo cameras converge (e.g., the convergent plane), the artifacts may be determined to be defocused images of the object a distance away from the convergent plane (e.g., the retina). These objects may be scattering light, for example, from the crystalline lens, etc. Accordingly, these image features could be removed with image processing. Information from another camera can be used to fill in the area of the image where the image feature was removed from one camera image. For example, the information from the two images acquired by the two sensors 441, 442 should be sufficient. The removed portions of each of the two images are in different locations. Therefore after removing the artifact from one of the images, the missing part of that image after removing the artifact could be filled with information or portion of image from the other image. A similar approach can be performed as well on the other image when the artifact is removed therefrom. Such artifacts may include unwanted reflection, or haze, from the crystalline lens. Processing electronics may be employed to provide such an image processing capability.

Figure 5A:
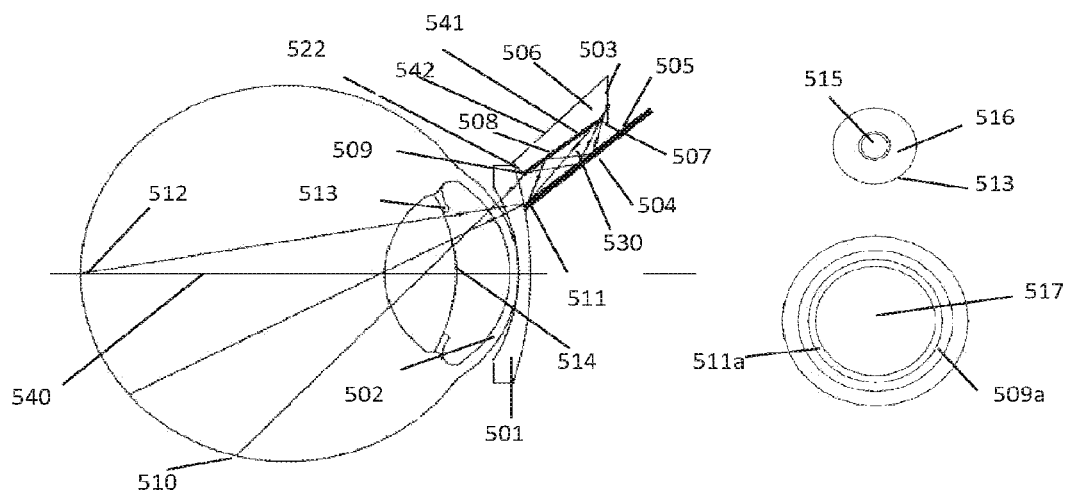
FIG. 5(A) schematically illustrates a light conditioning element of the eye imaging apparatus providing in some embodiments a light channel (e.g. hollow external channel) between said light conditioning element and sidewalls of an imaging lens.

FIG. 5(A) schematically illustrates a light conditioning element employed in various embodiments of the eye imaging apparatus. To obtain high quality images, proper illumination is provided through the proper portion of the natural opening of the eye while avoiding the imaging path. In particular, illumination is provided through the peripheral regions of the eye pupil. This approach reduces backscatter from the central portions of the pupil, which would degrade the image of the retina obtained by light reflected from the retina also passing through the pupil. Since the eye is a complicated biological organ with its own special optical systems, the scattering and reflection from the eye in combination with its small aperture cause significant difficulties in obtaining a high quality image. In particular, the reflection and scattering from the eye cause glare and haze, which obscures the images acquired by an eye imaging apparatus. Thus the images from the posterior segment of the eye with a wide field of view often exhibit a layer of strong haze or glare. This problem is especially acute for the patients with dark pigmentation in the eyes. Providing illumination through certain regions of the eye as described herein, however, can reduce this backscatter and reflection and the resultant haze and glare.

Figure 5B:
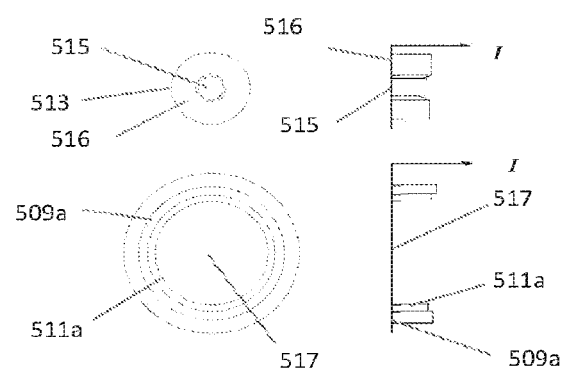
FIG. 5(B) schematically illustrates a light intensity profile on an optical window and the anterior surface of the crystalline lens provided by some embodiments for illumination.
Figure 5C:
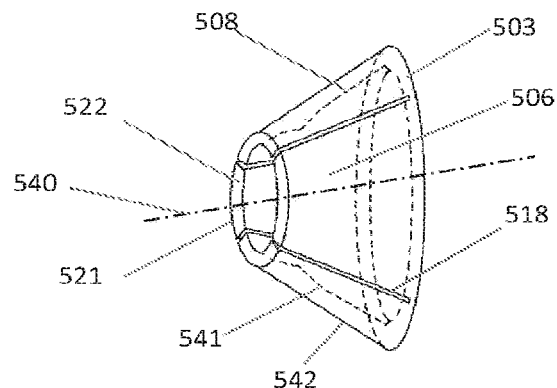
FIG. 5(C) schematically illustrates the three-dimensional view of the light conditioning element of the eye imaging apparatus for some embodiments.
Figure 5D:
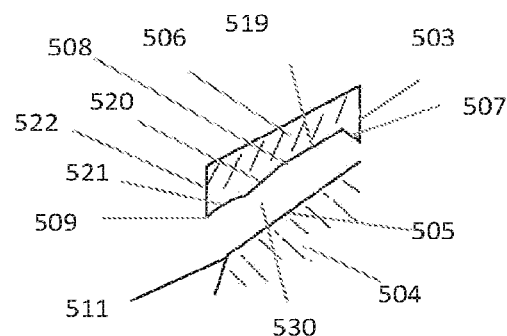
FIG. 5(D) schematically illustrates a close-up view of another embodiment of the light conditioning element having a multi-segment surface and a light channel (e.g. external channel) formed by said light conditioning element, and in particular by said multi-segment surface, and a sidewall of an imaging lens.

The light may be emitted from a light source (not shown in FIG. 5(A)) and injected into an optical light conditioning element 506 positioned behind the peripheral portion 509 of the optical window 501. FIG. 5(C) schematically illustrates a perspective view of the light conditioning element. The light conditioning element 506 has a hollow ring shaped body that is configured to be disposed about or around the imaging lens 504. In particular, the ring shaped body has an open region in which the imaging lens 504 or a portion thereof may be disposed. The light conditioning element is configured to provide a channel for light to propagate around the outside of the imaging lens 504 to the eye. The light conditioning element has a central axis 540, a front end and a back end with corresponding front surface 522 and back surface 503. The light conditioning element also has inner and outer side surfaces. The inner side surface 508 is closest to the imaging lens 504 and defines the open inner region in which the imaging lens 504 is disposed. In various embodiments, such as shown in FIGS. 5(A) and 5(D), the inner side surface 508 comprises a multi-segment surface. In some embodiments, the outer side surface comprises a multi-segment surface. Different portions or segments of the multi-segment surface have different features such as different shapes. In some embodiments different segments have different curvatures and/or angles of inclination. The different segments may also have different textures, coatings thereon, or comprise different material. In certain, embodiments, however, the different segments have different shapes to reflect and/or refract light incident thereon differently, for example, into different directions.

As illustrated in FIG. 5(C), the body of light conditioning element may comprise a hollow truncated cone-shaped solid structure comprising of solid optically transmissive or transparent material. However, in certain embodiments the light conditioning element comprises opaque material. Accordingly, the light conditioning element may comprise glass, plastic, ceramic, metal or combinations thereof. Other materials may also be employed. This shape may be characterized as a hollow and ring-shaped and frusto-conical. The front surface and the back surface as well as cross sections orthogonal to the length are in the shape of a circular ring. The back surface has a larger lateral extent, e.g., inner and outer radii than the front surface. FIG. 5(D) illustrates a cross-section view of the light condition element in some other embodiments. Although FIG. 5(A) and FIG. 5(D) illustrate the cross-section view of the light conditioning element in certain embodiments, the light conditioning element can be rotationally symmetric about the central axis 540 of the light conditioning element. In various embodiments, each segment of the multi-segment surface is annular and symmetric about the central axis. In various embodiments, the light condition element comprises a hollow rotational symmetric ring, where the inner surface of the ring comprises different segments instead of one smooth surface.

As discussed above, at least one of the surfaces of the light conditioning element comprises a multi-segment surface having multiple reflective and/or refractive segments. The different segments in the multi-segment surface may have different orientations, different shapes, different coatings, or any other different configurations. In some embodiments, the size of the segments in the multi-segment surface varies between 0.05 mm or 0.1 mm to 1 mm or 2 mm along a direction of the central axis. It is also possible for the size of the segments to be other values. In some embodiments, the total number of segments in one light conditioning element is greater than 2, but less than 10, or 20. Other number of segments is also possible. In various embodiments, the majority of the segments comprise reflective segments (e.g., having a reflectivity of at least 80%, 90%, 95%, 99%, or 100% and ranged therebetween) that reflect light from the light sources to the eye. In various embodiments, the multi-segment surface comprises a substantially specularly reflective surface. Accordingly, in various embodiments the multi-segment surface does not comprise a microstructured refractive diffuser. The multiple reflective surface segments are configured to provide precise directional control of light, thus in various embodiments the light conditioning element is configured to have a higher energy efficiency than a refractive diffuser. In certain embodiments, for example, the efficiency of the light conditioning element is 50%, 60%, 70% or higher or ranged therebetween.

The light conditioning element may distribute light received from the light source into different portions as a result of the different segments in the multi-segment reflective and refractive surface. In some embodiments, light from the light source that is reflected from the multi-segment light conditioning element is distributed the light into different portions by total internal reflection and possibly refraction of the multi-segment surface. In some embodiments, the light conditioning element distributes the light from the light source into different portions for example by total internal reflection and refraction of the multi-segment surface. The light conditioning element may provide a light channel 530 for propagation of light. In various embodiments such as shown in FIGS. 5(A) and (D), the light channel 530 is formed by the an inner surface 508 of the light conditioning element and an outer surface or sidewall 505 of the imaging lens 504. In some embodiments, this hollow external channel 530 is configured to receive light from the light source and direct the light to the eye. The light channel 530 may be considered an external light channel because this channel is formed in an open space between the inner surface 508 of the body of the light conditioning element and the side surface of the imaging lens 504. In other embodiments, the light channel may be formed between the two side surfaces of the body of the light conditioning element and be referred to as an internal light channel. In either case, at least one of the surfaces forming the channel may comprise a multi-segment surface. Such a multi-segment surface may distribute the light into the eye in the desired manner. Various embodiments include both an external light channel and an internal light channel.

In the embodiment shown in FIGS. 5(A) and 5(D), the light conditioning element is configured to direct a first portion of light from the inner edge of the light channel to a first area of a retina of the eye including an optical axis of the optical imaging system. In various embodiments, the first area comprises one-third of the field of view of the optical imaging system. When the optical axis of the optical imaging system is aligned with the optical axis of the eye, the first area is the central area of the retina of the eye. In various embodiments, the light conditioning element is configured to direct more than 50%, 60%, 70% and 80% of the light exiting from the inner edge of the light channel to the first area of the retina. The light conditioning element is also configured to direct a second portion of light from the outer edge of the light channel to a second area of a retina of the eye away from the optical axis and on an opposite side of the optical axis from the outer edge of the light channel from which the light is ejected. The second area is farther from the optical axis than two-third of the field of view of the imaging system. When the optical axis of the optical imaging system is aligned with the optical axis of the eye, the second area is the peripheral area of the retina. In various embodiments, the light conditioning element is configured to direct more than 50%, 60% and 70% of 1 the light exiting from the outer edge of the light channel to the second area of the retina. In various embodiments, the first portion of light forms an angle with the optical axis of the optical imaging system from +10 degree to −30 degrees, and the second portion of light forms an angle with the optical axis from −30 degree to −90 degrees. In this case, the plus degree corresponds to light traveling upwardly from the optical axis shown in FIG. 5(A), and the minus degree corresponds to light travels downwardly from the optical axis. In various embodiments, the direction of the optical axis of the optical window is the same as the central axis 540 of the hollow cone-shaped solid structure and the two axes may be aligned in certain embodiments. In various embodiments, the light conditioning element is configured to direct more than 50%, 60%, 70% and 80% of the light exiting from the inner edge of the light channel to propagate with a first angle between +10 degree to −30 degree with respect to an optical axis of the optical imaging system. In various embodiments, the light conditioning element is configured to direct more than 50%, 60%, and 70% of the light exiting from the outer edge of the light channel with a second angle between −30 degree to −90 degree with respect to the optical axis.

As illustrated by FIG. 5(A), in various embodiments, the light conditioning element is configured to direct light outside an imaging path of the optical imaging system at the cornea and optical window. As a result, less backscatter is generated from the cornea and optical window that is in the imaging path. The image of the retina relayed to the sensor therefore has reduced haze and glare.

Also as shown in FIGS. 5(A) and 5(D), in various embodiments, the eye imaging apparatus may include a hollow external light channel 530 formed between the multi-segment surface 508 of the light conditioning element 506 and the side surface of the imaging lens 504. The light conditioning element 506 may include an optical reflective (and potentially refractive) multi-segment surface which splits the light from the light source into different portions, by reflection, e.g. total internal reflection, (and potentially refraction) of its multi-segment surface. The multi-segment surface 508 may be suspended with proper space from the side surface of the imaging lens 504 to form an external light channel 530. In certain embodiments the inner surface of the light conditioning element and the outer surface of the imaging lens are spaced apart by less than or equal to 3.0 mm, 2.5 mm, 2.0 mm, 01.5 mm, 1.0 mm or 0.5 mm and larger than zero or ranges therebetween, such as for example, between 3.0 and 2.0 mm or between 2.5 mm and 1.5 mm, etc. in certain embodiments of the invention. Separations outside these ranges are also possible. In various embodiments, the side surface of the imaging lens 504 comprises a first layer or coating of an optically absorptive material and a second layer or coating of an optically reflective material 505 on the top of the absorptive coating. Such multilayer coating produces strong absorption to the stray light within the imaging lens 504, while reflecting illumination light from another side of the coating. However, other configurations are possible.

Accordingly, with continued reference to FIGS. 5(A) and 5(D), in various embodiments, light is injected into the rear portion of the light channel farther from the transparent window. This light propagates through the light channel possibly reflecting from the coated sidewalls of the imaging lens and the multi-segmented inner surface of the light conditioning element. Light in the light channel may propagate to the forward portion of the light channel, which is closer to the transparent window and exit the light channel.

In various embodiments, after multiple reflections (and possibly refraction, for example, at the transmissive segment 507), a portion of the light is propagated through the outer edge 509 of the external light channel (see, e.g., 5(D)), the optical window 501 and the cornea 502, and onto a second area 510 of a retina of the eye away from the optical axis and on an opposite side of the optical axis from the outer edge of the light channel. The second area 510 is farther from the optical axis than two-third of the field of view of the imaging system. When the eye is aligned with the optical axis of the optical imaging system, the second area 510 is the peripheral area of the retina. This light exits the channel after reflecting from the inner surface of the light conditioning element. For example, the last reflection prior to exiting the light channel is from the inner surface of the light conditioning element. The portion of light 509a emitted from the outer edge of the light channel may be directed at −30 to −90 degree with respect to the optical axis of the optical window and/or the central axis 540 of the light conditioning element. In various embodiments, most of the light from the outer edge of the light channel, for example 50%, 60%, 70%, 80%, 90%, 95% or more of the light or ranges therebetween, is directed into the peripheral portion, such as between −30 to −90 degree with respect to the optical axis of the optical window and/or the central axis 540 of the light conditioning element.

Another portion of the light exits the light channel at its inner edge 511 and is transmitted through the optical window 501, the cornea 502 and is incident on the first area 512 of a retina of the eye including an optical axis of the optical imaging system. The first area comprises one-third of the field of view of the optical imaging system. In some embodiments when the eye is aligned with the optical axis of the optical imaging system, the first area 512 is the central portion of the retina. This light exits the channel after reflecting from the outer surface of the imaging lens. For example, the last reflection prior to exiting the light channel is from the outer sidewall surface of the imaging lens. In various embodiments, the portion of light emitted from the inner ring edge of the light channel may be directed at +10 degree to −30 degree with respect to the optical axis. In various embodiments, most of the light from the inner edge 511 of the light channel, for example 50%, 60%, 70%, 80%, 90%, 95% or more of the light or ranges therebetween, is directed into the central portion, such as between +10 degree to −30 degree with respect to the optical axis.

As shown in FIG. 5(A), in various embodiments the design of the multi-segment surface as well as the location of the inner edge of the light channel 511 is such that the light emitted from this area is not blocked by the edge of the iris 513 of the eye, which may or may not be dilated during examination. Additionally, in various embodiments, the multi-segment surface and the light conditioning element are configured such that this light passes through the pupil of the eye more at peripheral locations of the pupil than at central locations of the pupil. In some embodiments, for example, most of the light from the light conditioning element does not pass through the eye pupil within an area corresponding to the optical imaging path so as to reduce the likelihood of back-scatter of incident illumination into the optical imaging path. In some embodiments this amount of light is more than 85%, 90%, or 95% or values therebetween. In many cases, the eye will be dilated using medication during the eye examination. In such cases, the pupil may be 6 to 8 mm for newborn babies, possibly 4 mm for premature babies or 5 mm for children. In contrast, the entrance pupil of the optical imaging system is about 1 to 2 mm in various embodiments. Accordingly, in certain embodiments most of the light from the light conditioning element propagates through the eye pupil or past the entrance pupil of the optical imaging system a distance of at least 2 mm or 2.5 mm to 3 mm or 3.5 mm from the optical axis of the eye imaging system or central axis of the light conditioning element. In some embodiments, this amount of light is more than 80%, 90%, 95%, 97%, 99% or values therebetween. Accordingly, this illumination light propagates into the eye at locations well outside the entrance pupil of the imaging system (which might be 1 to 2 mm in diameter) and only a negligible amount, if any, passes through the entrance pupil of the optical imaging system toward the retina. To further illustrate the illumination arrangement, a front view of the optical window 501 is provided as one insert in FIG. 5(A), where the light from the inner edge of the light channel forms a light ring 511a and the light from the outer edge forms a larger light ring 509a. The central portion 517 of the optical window 501 is reserved as the optical path for the light returning from the retina as the imaging light. In order to demonstrate the lighting condition on the optical window, the light intensity (I) profile on the optical window is schematically shown in FIG. 5(B). As shown in FIG. 5(A) and FIG. 5(B), the illumination path and the imaging path are essentially separated at the optical window 501.

As discussed above, in some embodiments, the optical imaging system forms an entrance pupil near the crystalline lens of the eye. A front view of the anterior surface of the crystalline lens is also shown in the other insert of FIG. 5(A), where the entrance pupil 515 is located near the center of the iris 513. The illumination light from both the outer and inner edges of the light channel 509, 511 falls on the area 516 which is outside of the entrance pupil 515 of the optical imaging system, and does not fall onto a circular area on the cornea or at the optical window (e.g., the front surface thereof closest to the eye) and entrance pupil located near an optical axis of the optical window. Accordingly in various embodiments most of the light (e.g. a value greater than 50%) from the light conditioning element does not fall within the entrance pupil of the imaging system as this light propagates to the retina. In some embodiments, this value is at least 70%, 80%, 85%, 90%, or values therebetween. Similarly, in various embodiments most of the light (e.g. a value greater than 50%) from the light conditioning element does not fall within the optical path of imaging system at the cornea or optical window (e.g., the front surface thereof closest to the eye) as this light propagates to the retina. In some embodiments, this value is at least 70%, 80%, 85%, 90%, or values therebetween. In order to demonstrate the lighting condition on the anterior surface of the crystalline lens, the light intensity (I) profile of the illumination light is also schematically illustrated in FIG. 5(B). Such optical arrangement creates a separation between the illumination path and the imaging path on the cornea, optical window (e.g., the front surface thereof closest to the eye), and an anterior surface of the crystalline lens and in some embodiments at the entrance pupil of the imaging system, and reduces or prevents the reflected and scattered light from entering the imaging path and eventually the image sensor. As seen in FIG. 5(B), a small border area may be created between the illumination zone 516 and entrance pupil 515, thus further reducing the cross talk. The width of the border area is less than 0.5 mm. As discussed above, the illumination light from the inner edge 511a of the light channel is projected to the central portion of the retina while the light from the outer edge 509a is projected to the peripheral area. In various embodiments, the light from the two light rings 509a, 511a of the optical window 501 may produce an overlapping area for the illumination at the retina, and form a relatively uniform illumination condition.

As illustrated, in various embodiments, the optical window is disposed forward the imaging lens and forward the light conditioning element. In certain embodiments, the optical window may be dropped in from inside the housing during the assembly (for example, from the rearward direction as opposed to from the forward, eye side direction). In some embodiments, the size of the optical window is such that the peripheral portions of the optical window extend forward and in front of the light conditioning element. Light from the light conditioning element directed toward the eye may be transmitted through the peripheral portions of the optical window to the eye in various such embodiments. In certain embodiments, the size of the optical window is smaller and light from the light conditioning element directed toward the eye is not transmitted through the peripheral portions of the optical window to the eye.

FIG. 5(D) schematically illustrates a cross-sectional view of another embodiment of the light conditioning element depicting the external light channel formed by the inner surface of the light conditioning element, which is shown as a multi-segment surface, and the outer sidewall of the imaging lens. The hollow truncated cone shaped device 506 may comprise optically transmissive or transparent material. Some portion of its surfaces may be optically polished. In some embodiments, the surface 507 may be left uncoated or coated with optical transmission enhanced coating and may potentially redirect light by refraction. The multiple segments 519, 520, 521, and 522 of the surface 508 may be coated with optically reflective coating. The segment 521 of the surface may be in the shape of a spherical or non-spherical curved surface as may be the other segments in different embodiments. The light from the light source enters the external light channel formed between the light conditioning element 506 and reflective surface 505 of the imaging lens 504. Some portion of the light may be blocked and reflected by the reflective surface 519. Some portion of the light may be reflected by the surface 505 first, then be reflected by the surface segment 520, and then be reflected by the surface 505 the second time, eventually being emitted from the inner edge 511 of the light channel and projected onto the central area of the retina near the optical axis of the eye and the imaging system. Some portion of the light, which may be reflected by the surface 505 and then be reflected by the surface 521, may be emitted from the outer edge 509 of the light channel and projected onto the peripheral area of the retina across the optical axis of the eye and the imaging system. A portion of the light, which may be reflected by the surface 505 only once and then exits the light channel, may eventually be projected onto the retina between the central area and the peripheral area in various embodiments. Ray tracing simulations can be used to design such multi-segment surfaces.

Figure 5E:
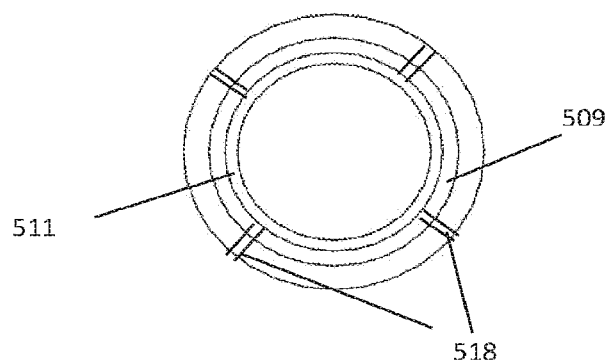
FIG. 5(E) schematically illustrates the light conditioning element comprising multiple sections in some embodiments.

FIG. 5(C) and FIG. 5(E) schematically illustrates a light conditioning element comprising multiple sections or pieces spaced apart, for example, by multiple gaps. The light conditioning element is configured to provide enhanced illumination in a sequential illumination method which will be discussed below. As shown in FIG. 5(E), multiple gaps 518 or barriers are used to separate the light conditioning element into multiple sections. The barriers could comprise light blocking (e.g. opaque) ribs or portions inside the light channel, or light absorbing strips or portions in the inner surface of the light conditioning element, to have same optical effects. For example, the light conditioning element may include four equal sized sections. The separations between the sections prevent the light from entering one section of light conditioning element from another. These separations may comprise air gaps or may be filled with material such as opaque material or a combination thereof. In various embodiments, the locations and numbers of the sections may correspond to the numbers of light emitting elements used in sequential illumination method. For example, the arrangement of the light conditioning element shown in the FIGS. 5(C) and 5(E) is configured to work with the illumination system with 4 light emitting elements. Although the light conditioning element is shown to have four sections, the light conditioning element may comprise more or less sections or pieces. Although equal size sections are shown in FIG. 5(E), in some embodiments, sections having unequal size may be used. Also, although FIG. 5(E) shows four completely separate pieces, in some embodiments elongate slits can separate the sections but the light conditioning element may nevertheless comprise a single unitary piece, the four sections being defined by slits that do not completely separate the sections into separate pieces. Similarly, various combinations may be employed. For example, the light conditioning element may comprise two pieces, each having such a slit thereby providing two separate sections per piece for a total of four sections, and other configurations are also possible.

Figure 6:
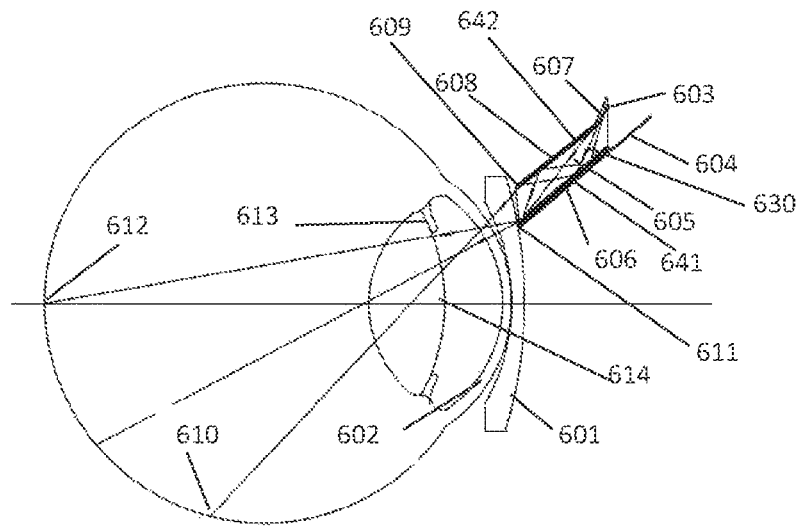
FIG. 6(A) schematically illustrates the light conditioning element including an internal light channel which can be used in some embodiments.
FIG. 6(B) schematically illustrates a close-up view of another embodiment of the light conditioning element comprising an internal light channel having multi-segment surfaces on opposite sides of the channel.
Figure 6:
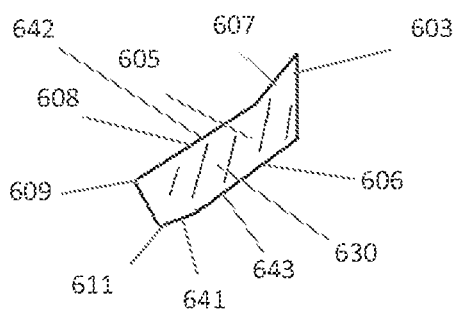

The light conditioning element may take many different forms, yet still produce the same or similar results in various embodiments. Some embodiments of the light conditioning element are schematically illustrated in FIG. 6(A) and FIG. 6(B). The light conditioning element 605 may comprise solid optically transmissive or transparent material (which may comprise glass or plastic) with two side surfaces, an inner surface 641 and an outer surface 642, at least one comprising a multi-segment surface. The light conditioning element 605 comprises a light channel 630 formed by the two side surfaces 641, 642 of the solid optically transparent material, where the inner surface 641 may contact the side surface of the imaging lens. This light channel 630 within the light conditioning element 605 may be referred to as an internal channel. Light from the light source travels in the internal light channel within the solid optically transparent material. The multi-segment surfaces may include both reflective and refractive segments. In certain embodiments, two segments 606 and 608 are coated with optically reflective coating, while the remaining segments 607 is polished and optically transmissive. If the index of refraction of the solid optical transparent material is sufficiently high with respect to the surrounding medium or media, the reflective coating on the segments 606 or 608 may not be employed in various embodiments as light may be reflected by total internal reflection. Accordingly, the inner surface of the light conditioning element and the outer surface of the imaging lens are spaced apart by an air gap having a thickness less than or equal to 0.3 mm, 0.2 mm, 0.15 mm, 0.1 mm, or 0.05 mm and larger than zero or ranges therebetween, such as for example, between 0.3 and 0.1 mm or between 0.15 mm and 0.05 mm, etc. in certain embodiments of the invention. Separations outside these ranges are also possible. The outer side surface 604 of the imaging lens may be coated with optically absorptive material to absorb the stray light and/or reflective material in various embodiments. Either or both the light channel element and imaging lens may include one or more coatings that provide reflectivity and/or absorption.

In various embodiments, light from the light source enters the light conditioning element 605 when the light source is disposed against the light conditioning element 605 or light is directed into the light condition element using a lens, optical fiber, or other device. Some portion of the light may be blocked by the edge 607 of the reflective segment of the surface 608. In various embodiments, the majority of the light enters the internal light channel 630 formed by two multi-segment surfaces 606 and 608. For example, the surface 606 may comprise two segments 641 and 643 of the surface. In certain embodiments, a portion of the light, which is reflected by surface 606 and then by the surface 608 and then the surface 606 again, exits near the inner edge 611 of the light channel and is projected onto the first area 612 of the retina after passing through the optical window 601 and the cornea 602. A portion of the light, which is reflected by the surface 606 and then by the surface 608, exits near the outer edge 609 of the light conditioning element 605 and is used to illuminate a second area 610 of the retina across the optical axis 614 of the eye and the imaging system in some embodiments. A portion of the light, which is reflected by reflective surface 606 only once, may be projected onto the retinal between the first area and the second area. In various embodiments the first area of a retina of the eye includes the optical axis of the optical imaging system. This first area may comprise one-third of the field of view of the optical imaging system. When the optical axis of the optical imaging system is aligned with the optical axis of the eye, the first area is the central area of the retina of the eye. The second area of a retina of the eye is away from the optical axis and may be on an opposite side of the optical axis from the outer edge of the light channel from which the light is ejected. The second area is farther from the optical axis than two-third of the field of view of the imaging system. When the optical axis of the optical imaging system is aligned with the optical axis of the eye, the second area is the peripheral area of the retina. In certain embodiments, the optical arrangement for the illumination and the imaging paths on the cornea and the anterior surface of the crystalline lens of the eye is similar as shown in FIG. 5(A) and FIG. 5(B). In some embodiments, the light conditioning element including an internal light channel comprises a multi-piece device that includes multiple sections (and possibly gaps therebetween) such as illustrated in FIG. 5(E) to provide better illumination when a sequential illumination method is used.

Figure 7A:
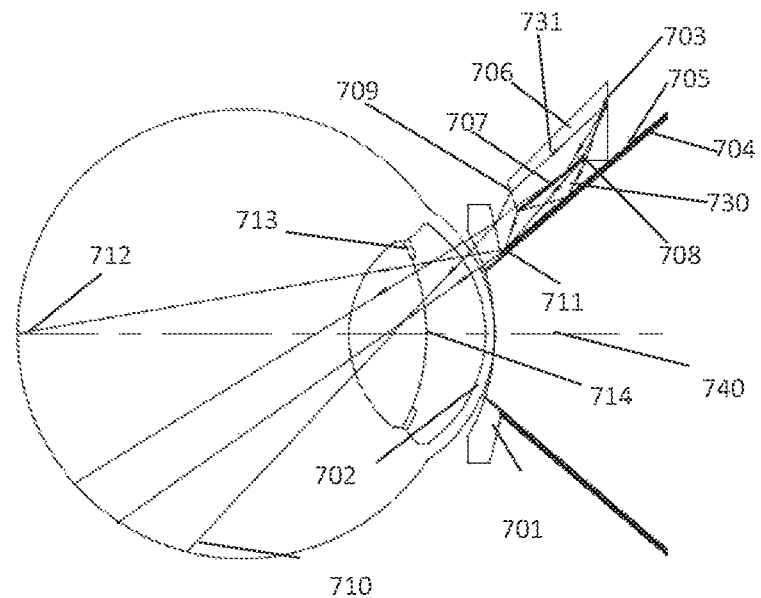
FIG. 7(A) schematically illustrates the light conditioning element comprising an internal light channel and additionally forming a light channel (e.g. hollow external channel) between the light conditioning element and the sidewall of an imaging lens that can be used in various embodiments of the invention.
Figure 7B:
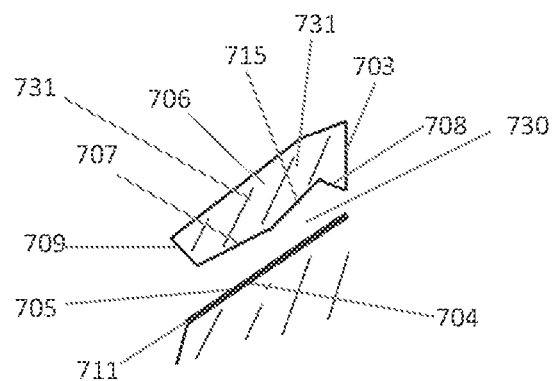
FIG. 7(B) schematically illustrates a close-up view of another embodiment of the light conditioning element comprising an internal light channel and forming an external light channel, the light conditioning element comprising a multi-segment surface on both the inner and outer sides.

FIG. 7(A) schematically illustrates some alternative embodiments of the light conditioning element providing a hollow external light channel and a solid internal light channel. FIG. 7(B) shows the close-up view of another embodiment of the light conditioning element 706 with multi-segment surfaces. The hollow external light channel 730 includes an inner reflective surface 705 formed by a side surface of the imaging lens and an outer multi-segment surface 707, 715 and 708 on the inner surface of the optical transparent material forming the light conditioning element 706. The light conditioning element 706 comprises a main body comprising optical transmissive or transparent material having an inner multi-segment surface 707, 715 and 708 and an outer multi-segment surface that together forms the internal light channel 731. In various embodiments, the inner multi-segment surface comprises segments of the surface 707 and 715 that are coated with a reflective coating such that the surfaces are reflective from both sides. Reflective coating may be employed in some embodiments when the index of refraction of the light conditioning element is low such that the total internal refraction is not sufficient. Reflective coating could also be employed when the refractive index is high. Additionally, in some embodiments the light conditioning element or portions thereof are coated with absorbing material to reduce stray light. In certain embodiments, the absorptive coating comprises epoxy with an index of refraction similar to that of the light conditioning element and with an added black absorptive dye. The remaining segments of the multi-segment surfaces are polished optically clear. The side surface of the imaging lens has a first layer of optically absorptive material 704 and a second layer of an optically reflective coating 705 thereon. The absorptive coating 704 is used to absorb the stray light inside the imaging lens while the reflective coating 705 is used to direct the light propagating within the external light channel 730.

After entering the light conditioning element 706, some portion of the light from the light source passes through the refractive segment 708 of the light conditioning element 706 and is reflected multiple times by two reflective surfaces 705 and 707. In various embodiments, a portion of the light is reflected by the coated outer sidewall surface 705 on the imaging lens first, then reflected by the inner multi-segment surface 707 of the light conditioning element, and then reflected by the coated outer sidewall surface 705 of the imaging lens again, exits near the inner edge 711 of the external light channel 730 and is eventually projected on to the first area 712 of the retina. Another portion of the light (not shown), which is reflected by the coated outer sidewall surface 705 of imaging lens only once, exits the external light channel 730 and is projected to the retina between the first area 712 and the second area 710. As in various embodiments, a portion of the light, which enters the internal light channel 731 of the light conditioning element 706 from the light source, is split into two parts. As shown in FIG. 7(A), a portion of light may be reflected by the inner surface 707 of the light conditioning element 706 before exiting the outer edge 709, while another portion of the light may directly exit the device 706 at the outer edge 709 of the light conditioning element 706 without reflection from the sidewalls thereof. Light exiting from the outer edge 709 as illustrated by rays in FIG. 7(A) may be directed toward the second area 710 of the retina. The first area 712 of a retina of the eye includes an optical axis of the optical imaging system. The first area 712 comprises one-third of the field of view of the optical imaging system. When the optical axis 714 of the optical imaging system is aligned with the optical axis of the eye, the first area is the central area of the retina of the eye. The second area 710 of a retina of the eye is away from the optical axis 714 and on an opposite side of the optical axis from the outer edge of the light channel from which the light is ejected. The second area 710 is farther from the optical axis 714 than two-third of the field of view of the imaging system. When the optical axis 714 of the optical imaging system is aligned with the optical axis of the eye, the second area is the peripheral area of the retina.

The optical arrangement for the illumination and imaging paths on the optical window 701 and crystalline lens of the eye is similar as shown in FIG. 5(A) and FIG. 5(B). In some embodiments, the light conditioning element may comprise a multiple pieces device, as shown in FIG. 5(E), comprising multiple section and multiple separations (e.g., air or material filed gaps) therebetween to sequentially provide different illumination patterns on the retina when a sequential illumination method is employed.

Various embodiments discussed above disclose a method of imaging an eye. The method comprises activating a light source to illuminate an eye, conditioning the light from the light source by a light conditioning element having at least one multi-segment surface and directing the conditioned light into the eye and onto the retina thereof, imaging the eye through an optical imaging system using light reflected from the retina, and receiving an image of the eye formed by the optical imaging system on an image sensor. The light conditioning element with a multi-segment surface is configured to receive light from the light source and direct light to the eye in an illumination pattern that, in various embodiments provide for illumination of peripheral sections of the retina. In some embodiments, the light conditioning element splits the light from the light source into different portions by reflection (e.g. total internal reflection) from and/or refraction caused by the multi-segment surface. The light conditioning element may be configured to direct a first portion of light from an inner edge of the light channel to a central area of a retina near an optical axis of the eye imaging apparatus, and direct a second portion of light from an outer edge of the light channel to a peripheral area of the retina away from the optical axis. To overcome the problems of scattering from the cornea and the anterior surface of the crystalline lens, the light conditioning element with a multi-segment surface may be configured to direct the light such that the light primarily falls outside the imaging path of the optical imaging system at the cornea and the anterior surface of a crystalline lens of the eye.

A variety of different types of optical windows may be used. As illustrated in FIG. 7(A), for example, the optical window has an open central aperture through which a front end portion of the imaging lens fits into. The optical window comprises annular or ring-shaped transmissive or transparent body. Light rays from the conditioning element pass through the annular body of the window. Light returned from the retina passes through the open central aperture into the imaging lens. The body of the optical window has front and rear curved surfaces. The front curved surface is concave and has a curvature to match the curvature of an eye, such as a human eye, so as to fit on the surface of the cornea. The rear surface, which is on the opposite side and farther from the eye, has a convex surface, although in other embodiments other shapes surfaces may be employed for either or both the front and rear surface of the optical window.

Although specific designs for the frontal optical window are shown in FIG. 5(A), FIG. 5(B), FIG. 6(A) and FIG. 7(A), the light conditioning element and the related illumination system discussed in each embodiment may be used in combination with other types of frontal optical windows.

Figure 8:
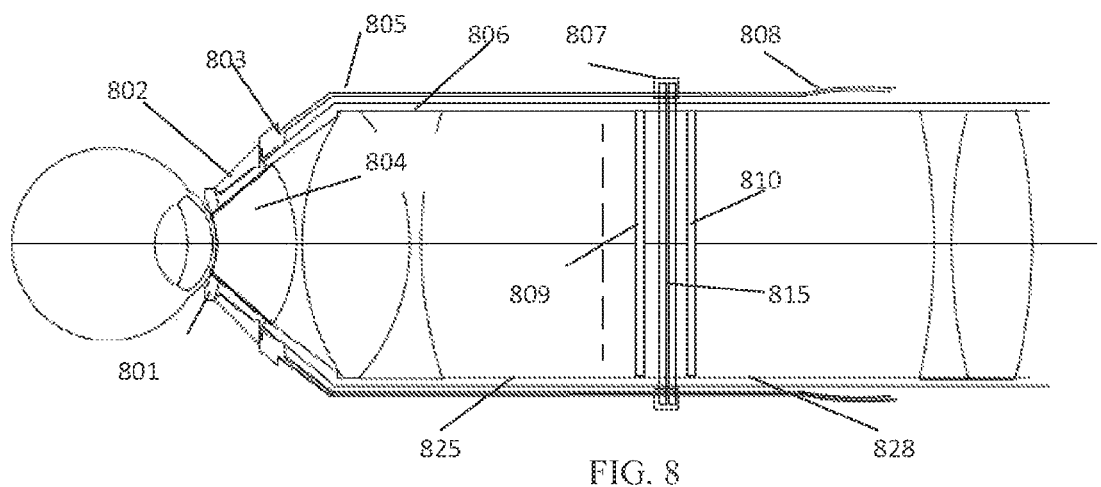
FIG. 8 schematically illustrates one embodiment of the eye imaging apparatus using light emitting elements such as LEDs as the light sources.

FIG. 8 schematically illustrates one embodiment of the eye imaging apparatus using light emitting elements as the light sources. The light source of the eye imaging apparatus may emit light in the visible spectrum, IR spectrum, near IR spectrum and/or UV spectrum. In some embodiments, the light source may include a plurality of light emitting elements. The light emitting elements may include solid state light emitters such as light emitting diodes and/or any other elements that are capable of emitting light. The light emitting elements may be compact, highly efficient and driven by low voltage. The light sources 803 may be placed directly against the light conditioning element 802. The light sources 803 may include the light emitting elements and the heat sink which is used to disperse the heat generated by the solid state emitting devices. The light from the light sources is directed into the posterior segment of the eye through the light conditioning element 802 and optical window 801 in the manner such as discussed above. The light sources, together with the heat sinks, are placed outside an inner casing or shell 806 which houses the optical imaging system including at least part of the imaging lens 804. This casing or shell may comprise, for example, a tube or ring. The light sources are powered electrically through the electric wires 805 laying along the outer surface of the casing 806. When the eye imaging apparatus comprises two separate modules such as a front imaging module 825 and a main module 828, which are separated at interface 815, one or more electric connectors 807 may be used to interconnect the wires 805 in or on the front module 825 and the wires 808 in or on the main module 828. In various embodiments, more sophisticated electronic drivers for the light sources 803 may be housed in the main module 828 in the right side of FIG. 8. The removable front imaging module 825, which is configured to be in contact with the cornea, may be built with various kinds of light emitting elements for a variety of illumination requirements and applications. For example, a first type of front imaging module may include light emitters having a first wavelength range and a second type of front imaging module may include light emitters having a second wavelength range different from the first. The first type of front imaging module can be interchanged with the second type of front imaging module or vise versa, for different applications, when they are connected with the main body 828 with common electric connector 807. A user may select which type of front imaging and conveniently remove and switch out the front imaging module 825 to another, which is conveniently attached onto the main module 828 by the user. In certain embodiments, the removable front imaging modules 825 may be driven by the same standard electronic drivers in the main module 828 through the electrical interconnector 807. To prevent dust from entering housings for the optics, two optical windows 809 and 810 may be used. In certain embodiments comprising a single unitary housing, however, as opposed to separate front imaging and main modules, the electric interconnection 807 and the optical window 809, 810 may be excluded.

Figure 9:
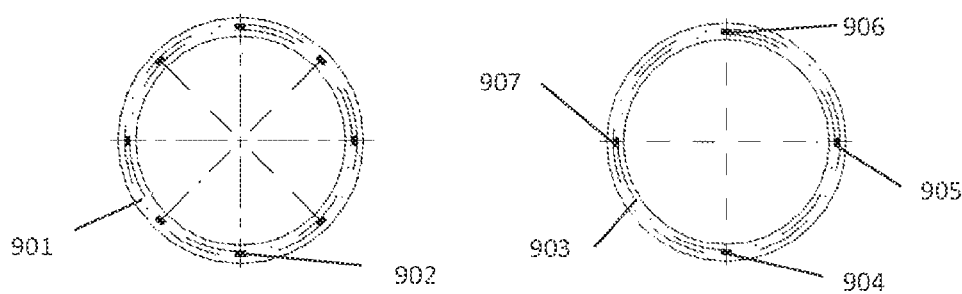
FIG. 9 schematically illustrates the distribution of the light emitting elements, where a total of 8 and 4 light emitting elements are used in respective embodiments.

In various embodiments, the location of the light sources may be distributed evenly to provide uniform illumination on the retina. The number of the light sources may vary, depending for example on the particular application. FIG. 9 schematically illustrates two embodiments of the distribution of the light emitting elements, where a total of 8 and 4 light emitting elements, respectively, are used. In one embodiment, the light emitting elements 902 is mounted onto a heat sink 901 that comprises a ring to increase its mass and heat dispersion capability. There are 8 light emitting elements 902 spaced evenly on the heat sink. The light emitting elements may be activated sequentially or simultaneously or be activated in any desired order. In various embodiments, the light emitting elements are also synchronized with the shutter of the image sensor. Drivers and/or a controller can be employed to control the timing of and/or sequence of illumination. Although 4 and 8 light emitters are shown in FIG. 9, more or less number of light emitting elements may be used. In some embodiments, sufficiently large numbers of emitters are employed such that the light sources form a "linear" line source. Such a "linear" line source may be curved and may form a ring centered about the optical axis of the imaging system, for example, in some embodiment. FIG. 9 shows an embodiment with 4 light emitting devices 904, 905, 906, 907 at 0°, 90°, 180°, and 270°, positioned on an annular heat sink 903.

An eye imaging apparatus with a wide field of view that employs sequential illumination as described herein is capable of overcoming scattering problems, and thus obtaining high quality images that are essentially glare or haze free. In some embodiments, the eye imaging apparatus comprises a light source disposed inside the housing wherein the light source comprises a plurality of light emitting elements configured to illuminate different portions of an eye time-sequentially. The image sensor is configured to receive a plurality of images of the eye with a same wide field of view through the optical imaging system while each portion of the eye is illuminated time-sequentially. In various embodiments, the eye imaging apparatus further comprises an image processing unit configured to generate a set of instructions to process the plurality of images to create a single clear image of the eye. In some embodiments, the eye imaging apparatus further comprises a memory configured to temporarily store the plurality of images, and a computing and communication unit configured to receive and transmit the plurality of images. The plurality of images may be transferred to other computing devices or interne based devices that include the image processing unit, which is configured to generate a set of instructions to process the plurality of images to create a single clear image.

Figure 10:
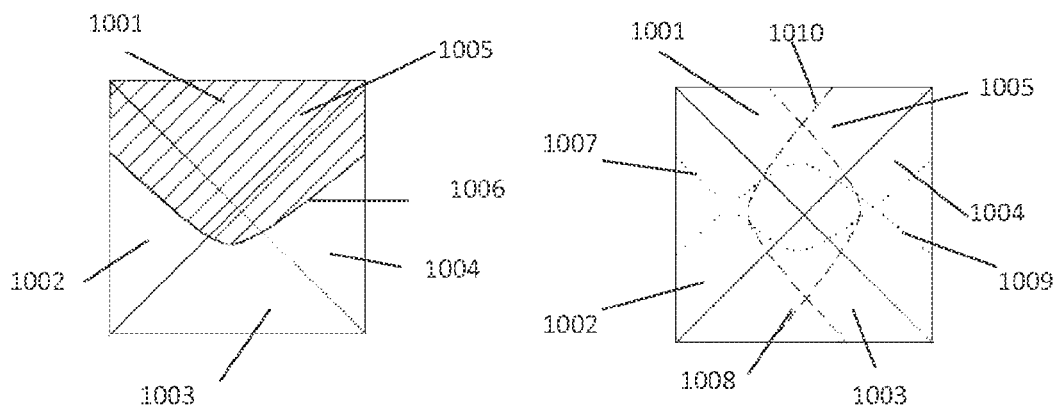
FIG. 10 schematically illustrates the images acquired when the light emitting elements are activated time-sequentially and a method used to enhance image quality according to various embodiments of the invention.

FIG. 10 schematically illustrates the example images acquired when the light emitting elements are activated time-sequentially and the method used to enhance the image quality according to various embodiments of the invention. A useful illumination condition is created when the light emitting elements are activated time-sequentially. For example, in an illumination system with 4 light emitting elements, if only one light emitting element is activated, then a first portion of the retina or the posterior segment of eye has increased illumination in comparison to other portions of the retina or posterior segment of the eye. At a later time if a second light emitting element is activated, a second portion of the retina or the posterior segment of eye has increased illumination in comparison to other portions of the retina or posterior segment of the eye including the first portion. Likewise at a later time if a third light emitting element is activated, a third portion of the retina or the posterior segment of eye has increased illumination in comparison to other portions of the retina or posterior segment of the eye including the first and second portions. Again, at a later time if a fourth light emitting element is activated, a fourth portion of the retina or the posterior segment of eye has increased illumination in comparison to other portions of the retina or posterior segment of the eye including the first, second, and third portions. In this example, where the retina is divided into four such sections, each of the four portions may be about 25% of the retina. However, in other embodiments the portion with increased illumination may be less than 50%, 40% or 30% but larger than 1%, 2%, 5%, 10% or 20% of the eye. In some embodiments, this portion is between 20-30%. Other values outside these ranges are also possible.

In various embodiments, this portion is on average illuminated more than other portions of the eye and has an average intensity greater than that of remaining portion or portions of the retina or posterior segment of the eye. Accordingly, only a portion of the example image 1001 acquired by the eye image apparatus is shown as having increased illumination in FIG. 10. In the example image 1001, the shaded area which is a bit larger than one quarter 1005 of the image has increased illuminated, while on average remaining quarters 1002, 1003 and 1004 are as well illuminated less. However, due to the unique scattering characteristic of the eye, the scattered light by the eye may show up mostly in the oppositely situated quarter 1003 in the form of haze or glare, leaving a clear portion in the primarily illuminated quarter 1005. The clear portion is essentially glare or haze free, or only has negligible glare or haze. Accordingly the quarter 1005, the clear portion, has substantially less glare or haze than the other portion. The brightness of the illuminated area often gradually decreases toward its boundary area 1006, while the brightness of image in the quarter 1005 is relatively uniform and with proper light exposure for the image sensor.

Accordingly, in various embodiments, the first portion (approximately a quarter) 1005 of the retina or posterior segment is illuminated, for example, by providing light from one of the light emitting elements while the other light emitters remain unactivated. Subsequently, another one of the light emitting elements is activated. As the next light emitting element is activated, the illuminated area is moved to be centered on another portion such as another quarter 1002 of the retina or posterior segment. Another image is captured. Next a third portion, for example, quarter, 1003 is illuminated by activating another of the light emitting elements. Finally, a fourth portion or quarter 1004 is illuminated by activating another of the light emitters and another image is capture. In such an example, each of the emitters is activated while the others remains unactivated. When all of the 4 light emitting elements are activated time-sequentially, 4 images with different quarters having increased brightness and clear portions are acquired.

The order of sequence can vary. Additionally, although activation of only one emitter at a time was discussed above, in certain embodiments, two are more light emitters are activated during the same time period. Additionally, although an image can be captured each time a different light source is activated, more than one image may also be recorded. Also, activating the light emitting element may comprise switching the light emitter on as compared to being off or otherwise increasing optical output therefrom for example significantly. Additionally, the light from the light emitting elements may be blocked, impeded, attenuated or redirected or otherwise modulated. In various embodiments, however, different portions of the retina or posterior segment are selectively illuminated more than other portions. The portion selected for increased illumination can be changed so as to provide increased illumination of the different portions at different times. Such selective illumination can be synchronized with the images captured at those times. Accordingly, images can be obtained at these different times and used to produce a composite image that has less haze and glare. In some embodiments, a driver and/or controller is used to activate the light emitters, direct light from a selected emitter or emitters and not from the others or otherwise selectively modulate the emitters. In some embodiments, simply more light from the selected emitter or emitters is provided in comparison to the other emitter. In certain embodiments shutters, light valves, and/or spatial light modulators are employed to control the amount of light from each of the light emitting elements. Although one emitter at a time was describe above as being activated, more than one light emitter can be activated at a time. In various embodiments, more light is provided by a subset of the total number of emitters so as to illuminate a portion of the retina or posterior segment or illuminate that portion more than one or more other portions. An image is recorded. Subsequently, a different subset of the total number of emitters is selected to illuminate another portion of the retina or posterior segment or illuminate that portion more than others. Another image is recorded. This process can be repeated multiple times in various embodiments. For example, 2, 3, 4 or more subsets may be selected at different times or for providing the primary illumination. Images of the eye may be obtained at the different times. These images or at least portions of these images may be employed to form a composite image of the eye, for example, of the retina and/or posterior segment. Accordingly, in various embodiments an imaging processing unit may be configured to generate a set of instructions to process the plurality of images to create a single clear image of the eye. Because the eye or the eye imaging apparatus may be moved slightly during the image capturing or imaging process, the plurality of images may not overlap precisely. The imaging processing unit may generate instructions to precisely align the plurality of images or portions thereof by analyzing the overlapping areas. Each of the plurality of images has a clear portion and an unclear portion. The clear portion of the image is essentially glare free or haze free, or has negligible glare or haze. The clear portion has substantially less glare or haze than the other portion, the unclear portion. The unclear portion exhibits glare or haze, which obscures the image. The imaging processing unit may further generate instructions to recognize the clear portion of an image in each of the plurality of images, remove an unclear portion and save the clear portion. The set of instructions may further include instructions to adjust the uniformity of the image brightness of the single clear picture near a border area to form a uniform brightness. The imaging processing unit is configured to combine the plurality of images to create the single clear image.

As shown in the example image 1001 in FIG. 10, for example, in an illumination system with 4 light emitting elements, when the quarter 1005 is well illuminated, the unclear portion of the image with glare is outside the boundary 1007. The unclear portion may be recognized and removed by a set of instructions from an image processing unit. Therefore only the clear portion of the image within the boundary 1007 is saved. Similarly, only the clear portion of the image within the boundary 1008 is saved when the quarter 1002 is well illuminated. Two additional images are acquired from the quarter 1003, 1004 and their surrounding areas which are within the boundaries 1009 and 1010, respectively. When all of the 4 light emitting elements are activated time-sequentially, 4 partial images are acquired.

Because the eye or the eye imaging apparatus may be moved slightly during the imaging process, the features from the 4 partial images may not overlap precisely. The extended area from the border of each quarter may be used to allow the proper adjustment and re-alignment of the images as set forth by the instructions from the imaging processing unit. After the 4 images are aligned precisely, the brightness of the images in the border area can be re-adjusted to produce one single clear image with uniform brightness.

In some embodiments, in order to align the images taken time sequentially, one or more additional images may be captured with all of the light emitting elements activated at the same time, in addition to the multiple images taken time-sequentially as described above. This image can be obtained using the same optical imaging system having the same field of view as was used to obtain the plurality of images obtained with time-sequential illumination. Although such image may be hazy or with glare, it may contain the unique graphic reference features, such as blood vessels, of the whole imaging area or the entire field of view. Using this image as a reference image to coordinate, each of the four partial images described above may be aligned with the reference image. The clear composite image could then be formed from the four images after proper adjustment of the locations.

Although in the example embodiment described above, a single reference image was obtained with all the light emitters activated to assist in alignment of the other images, in other embodiments less than all light emitters may be illuminated. For example, the light emitters for two quarters 1002, 1003 can be activated to align those quarters. Similarly, the light emitters for the other quarters 1004, 1005 can be activated to align those quarters. Additional images with less than all the light emitters can be activated to provide further alignment. For example, four reference images captured while illuminating different pairs of the four quarters may be used to align each of the four quarters and create a complete composite image.

Less reference images can also be used, for example, by illuminating more sections when capturing the reference image. In some embodiments, for example, a first reference image can be captured with three of the four quarters illuminated, and a second reference images can be captured with different three of the four quarters illuminated. Alignment can be provided using these first and second reference images. Other variations are possible. As discussed above, the number of sections illuminated and number of light emitters used to obtain the one or more reference images can vary.

Accordingly, one or more reference image can be employed to align images of sections obtained using time-sequential illumination. To generate a reference image, multiple sections are illuminated and an image is capture by the optical imaging system and sensor. This reference image will depict the sections and their positional relationship, and will contain reference features that can be used to align separate images of the separate sections. Although reference images can be obtained by illuminating all of the sections, not all the sections need to be illuminated at the same time to produce reference images that can assist in alignment. These reference images can be captured using the same optical imaging system having the same field of view as was used to obtain the plurality of images captured during time-sequential illumination. However, in alternative embodiments, reference images can be captured by other optical imaging systems and sensor. Additionally, reference images can be captured with using different fields-of-view. Other variations are possible.

An image processing unit may be utilized to process the images as set forth above to provide alignment. For example, the image processing unit may identify the reference features in the reference images to determine the positional relationship of the sections. The image processing unit may further align sections of images captured using time sequential illumination based on those reference features and the determined positional relationship of the sections.

In various embodiments, the rate of frequency of the time-sequential capturing is determined by the image capturing rate. In some embodiments, the imaging apparatus is configured to capture each image between 15 ms or 30 ms to 150 ms or 200 ms.

Accordingly, a method of imaging an eye by sequential illumination is disclosed to obtain high quality retinal images with a wide field of view. The method comprises activating a plurality of light emitting elements time-sequentially to illuminate different portions of an eye, imaging the eye through an optical imaging system and receiving a plurality of images of the eye through the optical imaging system and sensor while different portions of the eye are illuminated time-sequentially. The images are captured by the image sensor and processed to create a single clear image of the eye. The method may be used to digitally remove the unclear sections, thus reducing or removing the haze from the plurality of images obtained from the sequential illumination.

The sequential illumination method discussed in the previous paragraph may be applied when different numbers of the light emitting elements are used. The possible examples include 2 elements, 3 elements, 4 elements, 6 elements, 8 elements or even more elements. The light emitting elements need not be individually activated. In some embodiment, pairs may be activated at a time. Similarly, 3, 4, or more may be activated at a time. Other variations are possible.

Accordingly various embodiments comprise an eye imaging system comprising an eye imaging apparatus such as for example shown in FIG. 1(A) and FIG. 1(B), and an image computing module that includes another computing device or internet based device. The eye imaging apparatus may comprise a plurality of light emitting elements, an optical imaging system, an image sensor, memory and a computing and communication unit. In certain embodiments, the plurality of light emitting elements is configured to illuminate different portions of an eye time-sequentially. The image sensor is configured to receive a plurality of images of the eye with a same wide field of view through the optical imaging system as the different portions of the eye are illuminated time-sequentially. In various, although not all embodiments, the memory is configured to at least temporarily store the plurality of images captured by the image sensor. The computing and communication unit may be configured to receive and transmit the plurality of images. The eye imaging apparatus may further include a touch screen display to display the images. The image computing module may be configured to receive the plurality of images from and exchange data with the eye imaging apparatus. The image computing module may further include an image processing unit, which is configured to generate a set of instructions to process the plurality of images to create a single clear image of the eye. Other embodiments are also possible.

Figure 11:
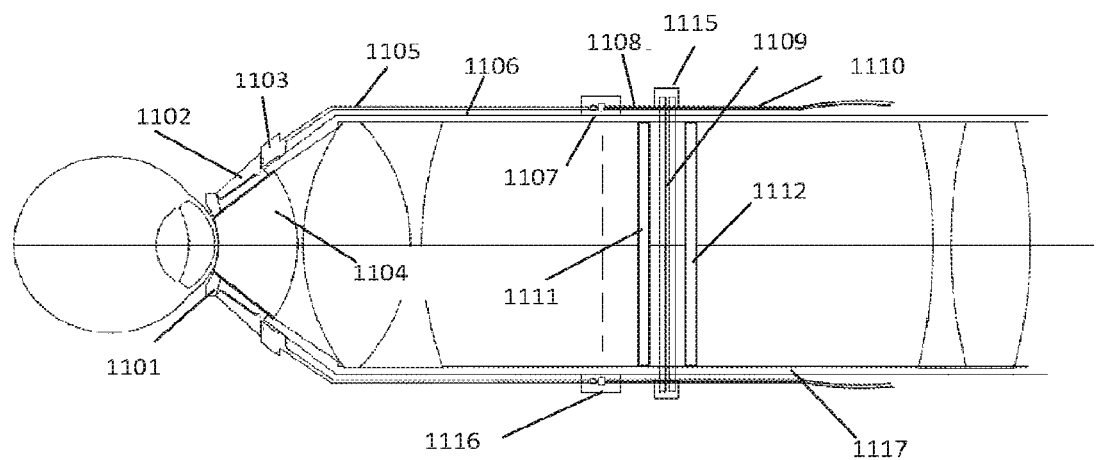
FIG. 11 schematically illustrates another embodiment of the eye imaging apparatus using optical fibers to guide light from the light emitting elements to the light conditioning element.

In some embodiments of the eye imaging apparatus, as schematically illustrated in FIG. 11, one or more optical fibers 1105 are used to guide the light from the light emitting element(s) 1107 to the light conditioning element 1102. In various embodiments, optical fiber bundles are used. The construction for the rest of the imaging apparatus is similar to the one shown in FIG. 8. When the eye imaging apparatus comprises two separate modules such as a front imaging module and a main module, which are separated at interface 1109, one or more electric connectors 1115 may be used to interconnect the wires 1108 in or on the front module and the wires 1110 in or on the main module. To prevent dust from entering the housings and depositing on the optics, two optical windows 1111 and 1112 are used to seal off the housings. If a single piece construction is required, then the electric interconnection 1115 and the optical windows 1111, 1112 can be excluded.

Figure 12:
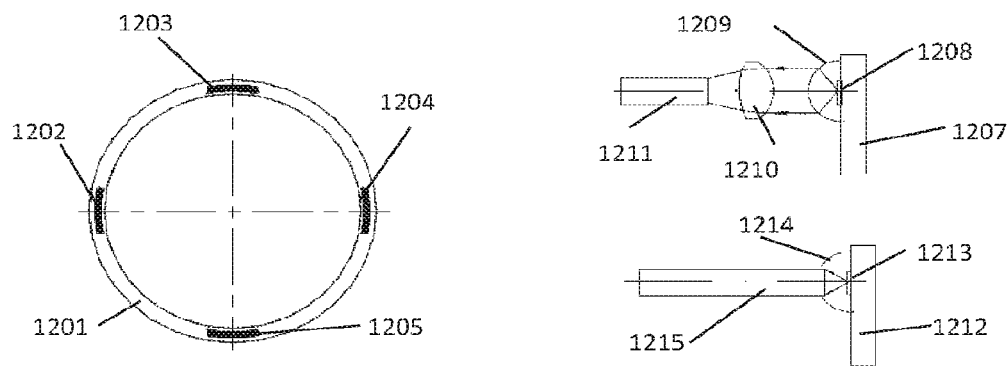
FIG. 12 schematically illustrates embodiments of light elements configured to couple light from the light emitting elements to the optical fiber lighting elements.

FIG. 12 schematically illustrates two embodiments of fiber optic couplers configured to couple light from the light emitting elements to the optical fiber. The optical fibers may be used to form multiple lighting elements that can be disposed against the light conditioning element. One example is schematically illustrated in FIG. 12, where optical fiber lighting elements 1202, 1203, 1204 and 1205 are incorporated into a lighting base 1201 and distributed evenly thereabout. The shape and size of each optical fiber lighting element shown in FIG. 12 is an example only and does other design can be employed. The number of the optical fiber lighting elements may be 4, 8 or any other number of lighting elements. As shown, continuous light sources, such as liner light sources, may be provided.

The lighting element such as for example lighting element 1202 shown in FIG. 12, receive light from one light emitting element. While two examples are shown in FIG. 12, other embodiments may be used to increase the optical coupling efficiency. In one embodiment, an optical coupling lens 1210 is used to collect light from the light emitting element 1208 and relay the light into the entrance of an optical fiber bundle 1211. The individual optical fibers in the bundle 1211 is then spread out at the another end of the fiber to form the lighting element. The light emitting element often comprises a protective dome 1209 and is mounted onto a ceramic or metal base 1207. The multiple light emitting elements may be mounted to a larger heat sink base 1116, as shown in FIG. 11, through their ceramic/metal bases, in order to increase the heat dispersion capability. The heat sink may also be in contact with the lens housing or casing, which is shown as 1106 in FIG. 11 of the imaging apparatus in order to disperse the heat. If the heat sink (ring) 1116 is built next to the interconnection surface 1109 as shown in FIG. 11, a pair of matching heat conducting surfaces comprising for example copper or other materials having good thermal conductivity may be built along the interconnection surface 1109, and as part of extension of lens housing 1106 and lens housing 1117 in the front and main modules of the imaging apparatus. When the removable front imaging module is attached to the main module of the imaging apparatus, the two heat conducting surfaces 1106, 1117 may contact each other, thus permitting transfer of the heat from the lighting elements to the larger mass in the main module. Such a design may reduce the temperature of the imaging apparatus housing, especially the housing of the removable front imaging module, which the user may employ to holds the imaging apparatus in various embodiments.

Also shown in FIG. 12, in some embodiments, the optical fiber bundle 1215 is directly inserted into the dome 1214 of the light emitting element 1213. The direct coupling may produce high efficiency, although the seal for the dome is penetrated which may have implications in certain situations.

Figure 13:
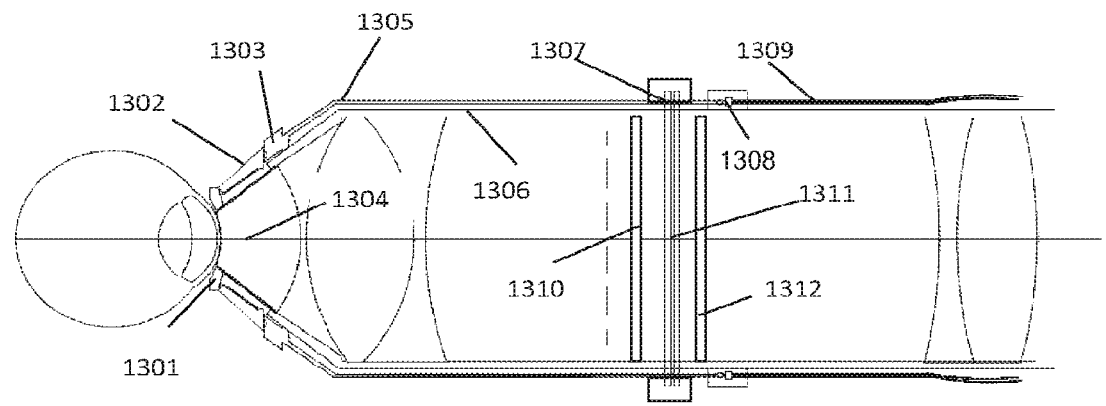
FIG. 13 schematically illustrates another embodiment of the eye imaging apparatus where the light emitting elements are placed in a main module of the eye imaging apparatus. Light from the light emitting elements is coupled to optical fiber bundles in the main module. Optical fiber bundles in a front imaging module are aligned and in direct contact with the optical fiber bundles in the main module to receive light therefrom.

In yet another embodiment shown in FIG. 13, the light emitting element 1308 is disposed in the main module of the eye imaging apparatus. The light is then guided to the light conditioning element 1302 through an optical fiber bundle 1305, which forms the new lighting element 1303. If the front imaging module is removable, then an optical coupler 1307 may be added to couple light from one side of interconnection 1311 to another. In certain embodiments, for example, two fiber bundles are aligned to each other, a first on the main module and a second on the front modules. The fiber bundles can be disposed so as to have ends that are in direct contact such that light can be coupled from the first fiber bundle into the second fiber bundle. The power of the lighting element 1303 is supplied through the electric wires 1309 by the electronic drivers.

Figure 14:
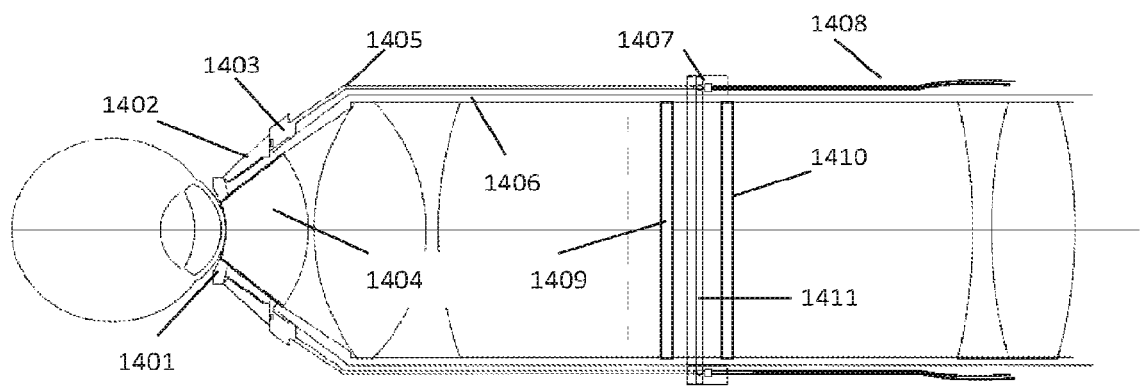
FIG. 14 schematically illustrates another embodiment of the eye imaging apparatus where the light emitting elements are located in the main module of the eye imaging apparatus, but near the interconnection interface and couple light into optical fiber bundles in the front imaging module.

Another coupling design is schematically illustrated in FIG. 14. A light emitting element 1407 is located in the main module of the eye imaging apparatus, but near the interconnection interface 1411. The light is coupled into an end of an optical fiber bundle 1405, which is located in the removable front imaging module of the imaging apparatus, with the end of the optical fiber bundle being exposed to the outside and facing the light emitting element 1407. The optical fibers in the bundle 1405, extend along the outside of the lens housing or casing 1406 and are used to form the multiple lighting elements 1403. The power of the light emitting element 1407 may be supplied through the electric wires 1408 from the electronic drivers.

Figure 15:
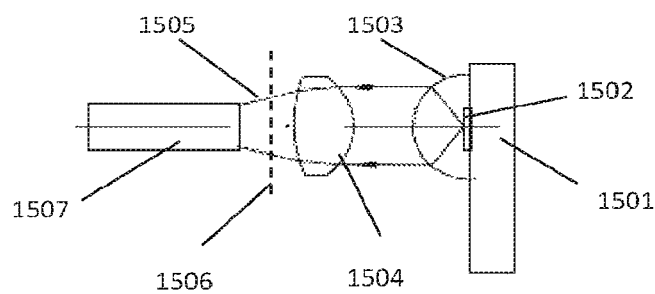
FIG. 15 schematically illustrates the details of the optical coupling design between the removable front imaging module and main module of the imaging apparatus according to various embodiments of the present invention.

One embodiment of the optical coupling design is shown in FIG. 15, where the dash line 1506 represents the interconnection interface between the two modules of the imaging apparatus. In various embodiments, the light from the light emitting element 1502 is initially collimated by a dome lens 1503. The collimated light is coupled to the fiber optical bundle 1507 through a coupling lens 1504. The light emitting element has a base 1501 that is mounted onto a heat sink base in the main module of the imaging apparatus. The coupling optical lens 1504 is also mounted in the main module and can be pre-aligned with the light emitting element 1502. Because the optical fiber bundle 1507 is located in the removable front imaging module of the imaging apparatus and does not come into physical contact with optics in the main module, the light 1505 is projected into the end of the fiber bundle directly through air or via free space. Such arrangement not only increases the optical coupling efficiency of the light, but also reduces wear at the end of the optical fiber bundles.

The light emitting elements in various embodiments may emit the light with broadband spectrum or narrow band spectrum. The light may be visible to the human eye with a single color or broadband, for example, a white color. The light may also be invisible to the human eye and be, for example, in the infrared, near infrared or UV range. All of the light emitting elements used in one unit may emit the same kind of light or different kinds of light.

In various embodiments, the light emitting elements emit white color light for color imaging applications. However, for certain applications, the light emitting elements may emit light in deep blue color, for example, when driven by the same electrical power supply system from the main module. The blue light may excite the fluorescin dye in the blood vessels of the eye, which in turn may emit green light. In certain embodiments, the optical window at the end of the removable front imaging module, such as 809 in FIG. 8, 1111 in FIG. 11, 1310 in FIGS. 13 and 1409 in FIG. 14, which is used to protect the optics from dust, comprises an optical blocking filter. For example, a green band pass filter may be employed. In such embodiments, the green emission light may be collected by the optics in the main module to form an image of fluoresin angiogram. The optical blocking filter reflects/absorbs the blue light, but allows the green and/or other emission light to be transmitted. The removable front imaging module with such features may be constructed as a fluoresin angiogram unit. Similarly, another type of angiogram imaging apparatus may be formed when the light emitting elements emit near infrared light and the optical blocking filter works in such spectrum too (for example, filters out near IE light). Accordingly, a filter that blocks the light produced by the emitters but transmits other, for example, longer, wavelengths, may be used to transmit fluorescent or other emission to the optical sensor.

Figure 16:
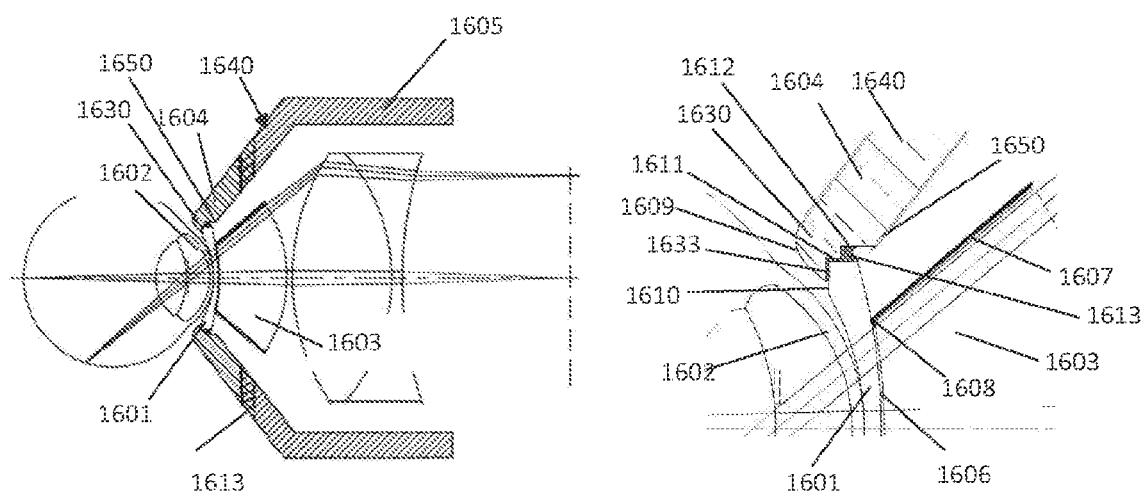
FIG. 16 schematically illustrates an embodiment of a hermetically sealed eye imaging apparatus where the optical window may be dropped in from inside the housing during the assembly process.

Because the optical window in the eye imaging apparatus is configured to be in contact with the patients, adequate sealing around the peripheral joint between the optical window and the housing can assist in reducing or preventing cross-contamination by the bacteria. FIG. 16 schematically illustrates one embodiment of a hermetically sealed eye imaging apparatus where the optical window may be dropped in from inside the housing during the assembly process. The optical window 1601 is in contact with the cornea 1602 of eye, but separated from the imaging lens 1603 with a small gap 1606. In various embodiments, the surfaces of the optical window 1601 and the imaging lens 1603 on both sides of the gap 1606 may have the same or similar radius of curvature. The gap 1606 may be filled with air or other optically transparent but mechanically elastic materials during the subsequent assembling process. Optical coatings may be applied to the optical surfaces on the both sides of the gap 1606 to reduce the optical reflectivity. The gap 1606 not only allows application of more sophisticated sealing technologies, but also adds a space for compensating for thermal expansion. In various embodiments, the gap 1606 between the optical window and the imaging lens adjacent thereto, for example, at the optical axis of the imaging lens, is between about 0.5 mm and 0.001 mm, or 0.3 mm and 0.001 mm although values outside this range are possible. The periphery of the imaging lens 1603 may be a conical or frusto-conical shape and may be coated with optically absorptive material 1607. The absorption spectrum of the optically absorptive material 1607 may be in the visible spectral range of the eye although the absorption spectrum may also extend into the invisible spectra. The absorptive coating 1607 may not only prevent the light from entering the imaging lens from outside, but also absorb the stray light from the eye when this light enters the imaging lens 1603 along with the light used for forming an image. A small opaque absorption ring 1608 may be added to the edge of the gap 1606 to prevent the light from entering the gap from the sides. The edge of the gap 1606 may also be simply filled with a small amount of optically absorptive material. The optical window 1601 is aligned with the rest of imaging optics with the help of the apparatus housing 1640, while the proper gap 1606 is maintained as a result.

The housing 1640 of the eye imaging apparatus comprise metal or other materials. The housing 1640 has a front end 1630 extends around the edge of the optical window 1601. The front end 1630 has a smooth front edge 1609 to prevent injury to the patients during the operation and to protect the optical window 1601 from scratching by hard foreign objects. A small flat surface 1610, in the form of a circular ring, may be disposed on the front peripheral area of the optical window 1601. This small flat surface 1610 may be near and/or extend from the side of the optical window 1601 to or near to the edge of the front concave surface of the optical window 1601. The front end 1630 of the housing 1640 is shaped and sized to fit with the profile of the optical window 1601 at the edge of the optical window, as shown in FIG. 16, and in various embodiments allows for various gaps between the housing 1640 and the optical window 1601. In various embodiments, an inner side surface 1650 of the housing 1640 comprises an alignment edge 1611 and a reservoir edge 1612 at the front end 1630. The optical window is separated from the alignment edge with a first gap which is horizontal and parallel to the side surface of the optical window. In various embodiments, the width of the first gap is between 0.3 mm and 0.01 mm or 0.2 mm and 0.01 mm. The alignment edge 1611 assists precision alignment of the optical window 1601 with the housing 1604 in directions normal to the optical axis. In various embodiments, the housing has an opening for fitting the optical window therein from the right hand side, as shown in FIG. 16, and for providing a gap, the first gap, between the optical window and the housing.

In some embodiments, the housing 1640 comprises a distal section 1604, which is a small housing, and a proximal section 1605, which is the apparatus housing. The proximal section comprise metal or other materials. The distal section, which may be a small housing, comprising the same or different metal material, in some embodiments, is connected to the proximal section 1605 by a bond. When the small housing 1604 is aligned with the apparatus housing 1605, then the optical window 1601, may, for example, be properly aligned with the optical axis of the imaging lens and imaging system. In various embodiments, the first gap provides for flow of hermetical sealing material as is discussed below. The opening bounded by the alignment edge of the housing is sufficiently large such that after the optical window is centered and aligned, the small first gap remains disposed between the housing and the window to allow for hermetic sealing material. To assist in placement of the optical window 1601 precisely along the optical axis and maintain a proper gap 1606, a small vertical surface is made in the frontal end 1630 of housing 1604, which creates a vertical gap 1633 between the housing and the small flat surface 1610 on the front peripheral area of the optical window 1601. In various embodiments, the width of the vertical gap is about between 0.3 mm and 0.01 mm or 0.2 mm and 0.01 mm. This vertical gap 1633 may permit the flow of hermetic material between housing and the small flat surface 1610 on the front peripheral area of the optical window 1601.

The optical window is also separated from the reservoir edge 1612 with a second gap. In various embodiments, the width of the second gap is about between 1.0 mm and 0.3 mm or 0.5 mm and 0.3 mm. The second gap may be larger than the first gap and configured to be a reservoir to be filled with a hermetic sealing material 1613. In various embodiments, when the hermetic sealing materials 1613 is melted under high temperature, the hermetic sealing material under the effect of gravity and surface tension force, also fills the smaller gaps, such as the first gap as well as the vertical gap between housing and the small flat surface 1610 on the front peripheral area of the optical window 1601 between the optical window 1601 and the housing 1640 to provide an air tight seal and strong bonding. The hermetic sealing material comprise material such as ceramic or metal that can, for example, be melted at very high temperatures and be caused to form an airtight seal that remains intact even when subjected to autoclave temperatures such as for example 120° C., 135° C., 140° C., or temperatures therebetween or potentially higher.

As illustrated, the front end 1630 of the housing 1640 where the optical window 1601 is disposed has vertical and horizontal edges, that with the help of an alignment fixture during manufacture and hermetic sealing material in the vertical and first gap, permit horizontal and vertical alignment, positioning, and proper orientation of the optical window in the imaging system. In this particular case, such vertical and horizontal edges of the housing form a corner in which the window surrounded by hermetic sealing material fits.

To match the thermal expansion properties of optical window material and the housing 1640, a special material may be used for the distal section 1604 of the housing 1640. In some embodiments, the whole housing 1640 may be made of the same material. In some embodiments, different materials may be used to make the housing. In various embodiments, the housing may comprise a distal section 1604, for example, a cap, and a proximal section 1605. The distal section 1604 is connected with the proximal section 1605 by a joint section 1613. In certain embodiments, for example, the distal section 1604, may comprise a first material such as titanium and the more proximal section 1605 of the housing comprises a second material such as aluminum. In certain embodiments, a distal section 1604 of the housing may be welded, bonded or otherwise connected together with a more proximal section of the housing 1605 at a joint section 1613. In various embodiments, the distal section of the housing can be bonded together with special treatment, such as explosion welding, to a portion of the joint section 1613 comprising the same material as the proximal section of the housing, the second material. For example, in the case where the distal section 1604 comprises titanium (first material) and the more proximal section comprises aluminum (second material), the joint section 1613 may comprise the aluminum (the second material). This aluminum (second material) in the joint section 1613 is bonded to the titanium (first material) using, for example, explosion bonding. The aluminum (second material) in the joint section is then bonded to the aluminum (second material) in the more proximal section of the housing for example laser welding. Other approaches to connecting the more distal and more proximal sections of the housing may be employed. In some embodiments, for example, the connection between the distal section 1604 of the housing and the more proximal section 1605 of the housing is filled with a hermetically sealing material. The material for the hermetically sealing could be, e.g., glass, ceramic, metal or adhesives. Such a technique may be employed, in some embodiments where the distal section of the housing comprises a different material than the more proximal section of the housing. In some embodiments, a special bonding section is introduced at the joint section 1613 in the form of a thin ring, which comprises two different materials. The front surface of the thin ring comprises the first material that may be welded with the distal section 1604, while rear surface of the thin ring comprises the second material that is then welded with the more proximal section 1605. The two materials (first material and second material) in the thin ring are bonded together with special bonding technique, such as explosion welding. In some embodiments, the distal section 1604 may simply be glued to the more proximal section 1605.

As illustrated in FIG. 16, as well as elsewhere (see, e.g., FIG. 1) in various embodiments, the housing is tapered and reduces in size closer to where the optical window is disposed and where contact with the eye/cornea is made. This tapered or sloping profile of the housing accommodates both the larger size of the relay lens and the smaller size of the window and imaging lens. As discussed above, the imaging lens may be frusto-conical and likewise be tapered as well, with the aperture size of the imaging lens being smaller closer to the eye than farther from the eye. In various embodiments, as shown in FIG. 16 and elsewhere, the bond, weld, or joint discussed above may be included in the front end where the housing is tapered.

In some embodiments a washer made of the same material as that of housing 1605 is included in the housing between the joint section 1613 and the proximal section 1605. The thickness of the washer is adjustable and permits the length of the housing in the longitudinal direction to be adjusted, which in turn controls the gap 1606 ultimately.

Figure 17:
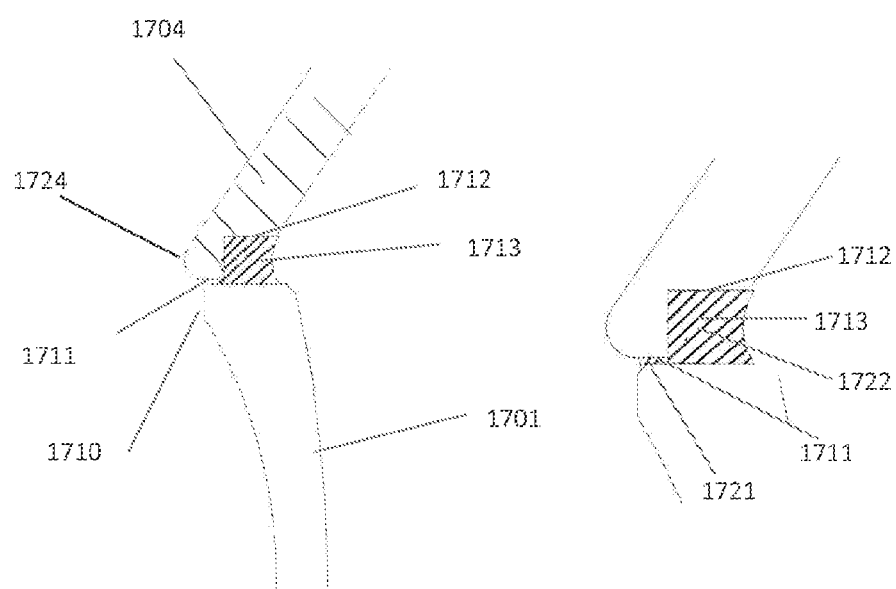
FIG. 17 schematically illustrates another embodiment of a hermetically sealed eye imaging apparatus.

FIG. 17 illustrates another embodiment of a hermetically sealed eye imaging apparatus. In this embodiment, the shape of the small housing, or the distal section, next to the optical window is modified from that in the embodiment shown in FIG. 16. The gap 1721 between the alignment edge 1711 and the edge of the optical window 1701 is reduced, which can provide both more precise optical alignment and a sufficient space to allow the free flowing of the hermetical sealing material from the reservoir 1713 through the narrow gap at the same time. The narrow vertical gap 1633 between the housing and the flat surface 1610 on the front peripheral area of the optical window 1601 shown in the FIG. 16 is removed. The removal of this narrow vertical gap 1633 and the full filling of the narrow gap 1721 between the alignment edge 1711 and optical window 1701 with the hermetical sealing material reduces risk of contamination problems. If the narrow vertical gap 1633 is not fully filled, for example the bacteria and other contaminants may hide inside and cause cross contamination between the patients.

As discussed above with respect to FIG. 16, in various embodiments, the housing shown in FIG. 17 has an opening for fitting the optical window therein and for providing a gap, the first small gap, between the optical window and the housing. Having such opening and a gap permits the optical window to be laterally translated and aligned, for example, using an alignment fixture that moves the lens laterally with respect to the housing. The optical window, may, for example, then be properly aligned with the optical axis of the imaging lens and imaging system when the housing is aligned with the rest of the imaging system. The first gap permits this lateral movement and alignment. Additionally, this first gap provides for flow of hermetical sealing material. Accordingly, the opening in the housing is sufficiently larger such that after the optical window is centered and aligned, the small first gap remains disposed between the housing and the window to allow for filling with the hermetic sealing material.

The optical window is also separated from the reservoir edge 1712 of the housing with a second larger gap 1722. The second gap 1722 may be larger than the first gap 1721 and configured to be a reservoir to be filled with a hermetic sealing material 1713. In various embodiments, when the hermetic sealing materials 1713 is melted under high temperature, the hermetic sealing material also fills the smaller gap 1721 between housing and the optical window 1701 to provide an air tight seal and strong bond. The hermetic sealing material 1713 may comprise material such as glass, ceramic or metal that can, for example, be melted at very high temperatures, for example, larger than 500° C. and caused to form an airtight seal that remains intact even when subjected to autoclave temperatures such as for example 120° C., 135° C., 140° C., or temperatures therebetween or potentially higher.

As discussed above, during the sealing operation, the alignment fixture holds the window into the center of opening of the housing where the window is inserted and, in certain embodiments, preserves a uniform gap around the periphery of the window. The alignment fixture also sets proper recess depth for the optical window by the small flat surface 1710 in reference to the front end 1724 of the small housing 1704, along the optical axis of the optical window. The viscosity of the hermetic material may be controlled so that the hermetic material wets both the window and the housing surface next to the gap and fills the first gap 1721 from the reservoir 1722, under the gravity and surface tension force. In various embodiments, the first gap 1721, which may be filled with hermetical sealing material 1713, is less than 1 mm or less than 0.2 mm although values outside this range are possible. In some embodiments, the thickness of first gap 1721 is made larger when approaching the space on the eye side, by the design of larger opening for the alignment edge 1711 and/or small 45 degree chamfer at the corner of optical window edge. As a result, when hermetic material is flowed through the first gap 1721, from the second gap 1722, the surface tension of the hermetic material will limit or stop the flow of the hermetic material into other surfaces on the eye side. In certain embodiments, the sealant not only seals the window, but also holds the window in the center of the opening of the housing.

Figure 18:
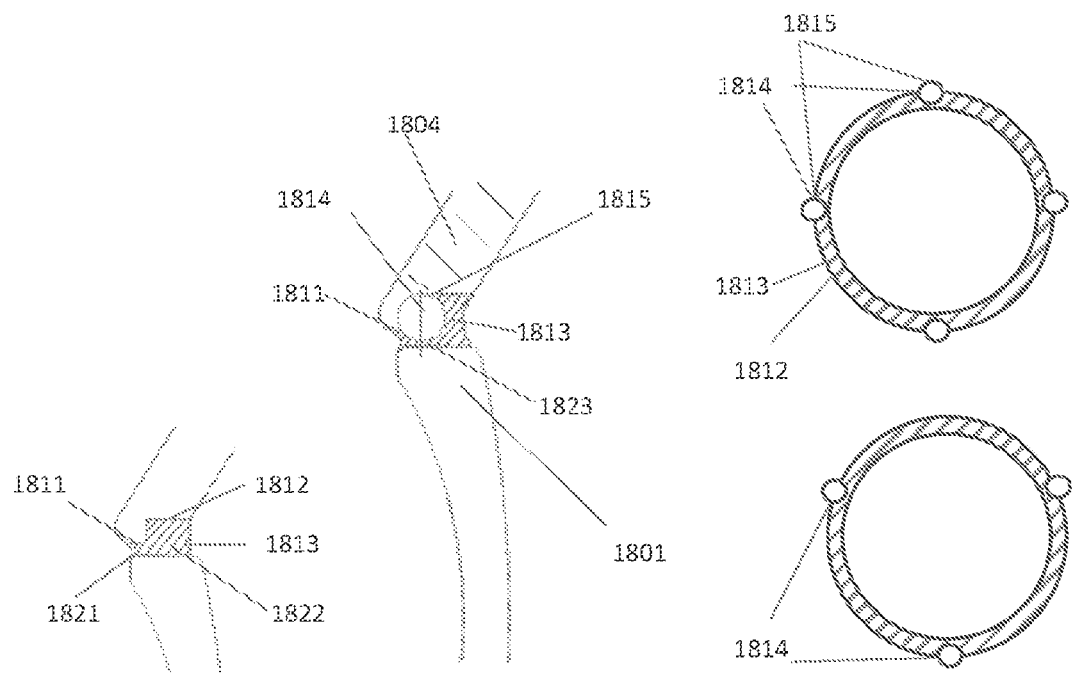
FIG. 18 schematically illustrates yet another embodiment of a hermetically sealed eye imaging apparatus comprising a plurality (e.g., or 4) tiny balls disposed with equal spacing around the peripheral of the optical window.

FIG. 18 schematically illustrates another embodiment of the hermetically sealed eye imaging apparatus. In this embodiment, a plurality of tiny balls 1814 are disposed with equal space around the periphery of the optical window and inside a plurality of bores 1815. The optical window 1801 is separated from an alignment edge 1811 of the housing with a first gap 1821. The optical window is also separated from a reservoir edge 1812 of the housing with a second larger gap 1822. This gap 1822 is configured to be the reservoir for the hermetically sealing material 1813. The balls 1814 are disposed in bores or boreholes 1815 drilled in the inner surface of the front end of the housing to accommodate the balls 1814. The bores 1815 have a diameter slightly larger than the second gap 1822 in order to enlarge the second gap 1822. Because of the increased size of the borehole 1815, the second gap 1822 is larger in the area surrounding the ball than in other areas where the ball 1814 is not positioned. The bore holes 1815 are disposed at a sufficient height such that a very narrow gap 1823 is disposed between the ball 1814 and the optical window 1801. This gap 1823 is beneath the ball 1814 as illustrated in the cross-sectional shown in FIG. 18. This narrow gap 1823 beneath the ball 1814 is narrower than the first gap 1821.

Such arrangement as describe above using balls 1814 as spacers with a gap between the ball 1814 and the optical window 1801 facilitates precise alignment between the optical window 1801 and the housing 1804. As discussed above, the housing has an opening for fitting the optical window therein and for providing the first and second gaps and in particular, the small gap 1823 between the optical window 1801 and the ball 1814 when the ball 1814 is in place in a borehole 1815. Having a larger opening and a gap permits the optical window to be laterally translated and aligned, for example, using an alignment fixture that moves the lens laterally with respect to the housing. The optical window 1801 may, for example, be properly aligned with the optical axis of the imaging lens and imaging system when the housing is aligned with the rest of imaging system. The small 1823 gap permits this lateral movement and more precise alignment.

Additionally, this small gap 1823 provides for flow of hermetical sealing material. Accordingly, the opening in the housing is sufficiently larger such that after the optical window 1801 is centered and aligned, the small gap 1823 remains disposed between the housing and the window 1801 to allow for hermetic sealing material 1813. A slightly larger gap 1821 between the edge of the optical window 1801 and the alignment edge 1811 of the housing (as compared for example to the first gap 1711 shown in the embodiment illustrated in FIG. 17) makes it easier for the hermetically sealing material 1813 from the reservoir 1822 to fully fill the gaps and space around the tiny balls 1814. As discussed above, in various embodiments, when the hermetic sealing materials 1813 is melted under high temperature, the hermetic sealing material 1813 also fills the smaller gap 1823 between balls 1814 and the optical window 1801 to provide an air tight seal and strong bond. The melted hermetic sealing material also forms a hermetic seal in portions of the larger gap 1822 elsewhere around the balls 1814 as well as where the balls 1814 are not disposed. The hermetic sealing material 1813 comprise material such as glass, ceramic or metal that can, for example, be melted at very high temperatures and caused to form an airtight seal that remains intact even when subjected to autoclave temperatures such as for example 120° C., 135° C., 140° C., or temperatures therebetween or potentially higher.

The layout with 3 and 4 balls are demonstrated in FIG. 18. These layouts show the arrangement of the balls, for example, as seen from the inside of the housing. These layouts, however, are to schematically illustrate where the balls are placed relative to each other. The number of the balls may vary including 3, 4, and other numbers. The spacer may be for example 0.5 mm in lateral extent such as diameter. Larger or smaller spacers may be used. The spacer, for example, may be as large as 1.0 mm and possibly 0.3 mm or smaller or any size between these values. Other sizes outside these ranges may also be possible. The spacers may comprise for example sapphire in some embodiments although other materials may be employed. In some embodiments, the balls may comprise the same material as the housing 1804 and/or the optical window 1801. The balls 1814 may also comprise materials that have a similar thermal expansion property as the optical window 1801 and/or the housing 1804. Spacer having shapes other than spheres can be employed. Cylindrically shaped spacers, for example, may be used. Additionally, the spacing can be different than shown in FIG. 18 and need not be evenly spaced.

In various embodiments, the diameter of the spacer, e.g., the ball, is selected to be slightly larger than the second gap. Therefore, when the bore is drilled, the outer edge of the bore extends beyond the outer edge of the second gap. Such arrangement prevents the balls from moving from of their location (e.g., in the bores) during the alignment and sealing operation. When the ball 1814 is placed in the bore 1815 and the window 1801 is inserted, a first side of the ball and the edge of the window provide the small gap 1823 while the second opposite side of the ball contacts the outer wall of the bore 1815. In various embodiments, the addition of the balls effectively reduces the space between the window 1801 and the housing 1804, and allows the hermetic material 1813 to flow easily in the large gap and the space between the balls. Also, with the spherical shape of the ball, the width of the first gap 1823 is widened on side facing the reservoir 1822 than the opposite side. As the result, the material can easily wet the surface of the ball and surround the ball within the material when the material is still in the fluid state.

Figure 19:
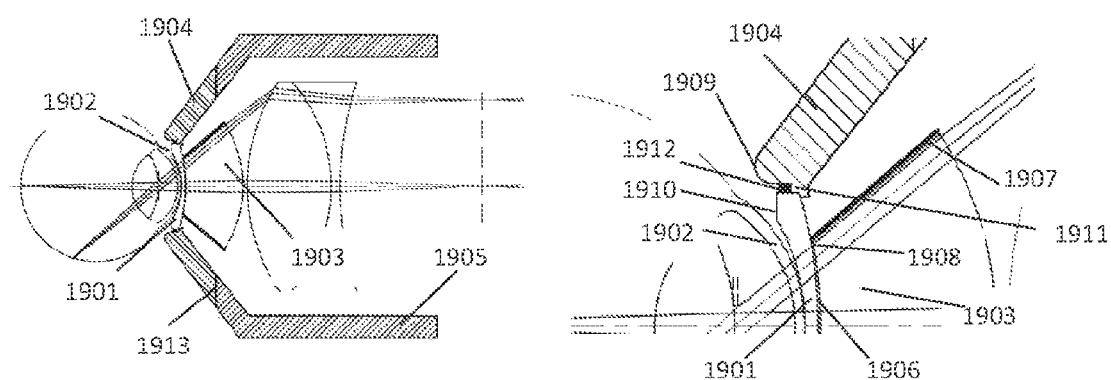
FIG. 19 demonstrates another embodiment of a hermetically sealed eye imaging apparatus where the optical window may be dropped in from the front side during the assembly process.

FIG. 19 demonstrates another embodiment of a hermetically sealed eye imaging apparatus where the optical window may be dropped in from the front side (eye side) during the assembly process. The hermetic sealing is applied between the optical window 1901 and the housing 1904. The embodiment has similar components as the embodiment shown in FIG. 16. For example, the imaging lens 1903, the absorptive coating 1907, the absorptive material 1908 and the gap 1906 function similarly as the imaging lens 1603, the absorptive coating 1607, the absorptive material 1608 and the gap 1606 respectively. Special bonding or welding process and design can be applied to the joint section 1913 in the embodiment shown in FIG. 19, as the joint section 1613 shown in FIG. 16. The optical window 1901 has a small flat surface 1910 disposed about the edge or periphery of the front concave surface of the optical window 1901. The use of the smooth corner 1909 at the front end of housing 1904 prevents potential injury to the patients during the operation. The optical window 1901 is designed to be dropped into the housing 1904 from the front side. A small alignment ring or edge 1911 is built into the housing 1904. The alignment ring 1911 includes a corner in which the edge of the optical window 1901 contacts. In various embodiments, the dimensions of the alignment ring 1911, and in particular the shape and size of the corner of the alignment ring 1911 are sufficiently similar to that of the edge of the optical window 1901 to provide a tight fit therebetween. As illustrated, the alignment ring 1911 has vertical and horizontal edges that permit horizontal and vertical alignment, positioning, and proper orientation of the optical window in the imaging system. In this particular case, such vertical and horizontal edges of the housing form a corner in which the window 1901 fits. Accordingly, the small alignment ring 1911 provides more precise alignment between the two components in comparison to an embodiment without the alignment ring. The larger gap between the two components is filled with the hermetically sealing material 1912 under high temperature. Such design not only provides air tight sealing to prevent growth of the bacteria in the small gap or cracks, but also enables strong bonding between the optical window 1901 and the housing 1904. An adhesive may also be used to seal the optical window 1901 in this embodiment.

Figure 20:
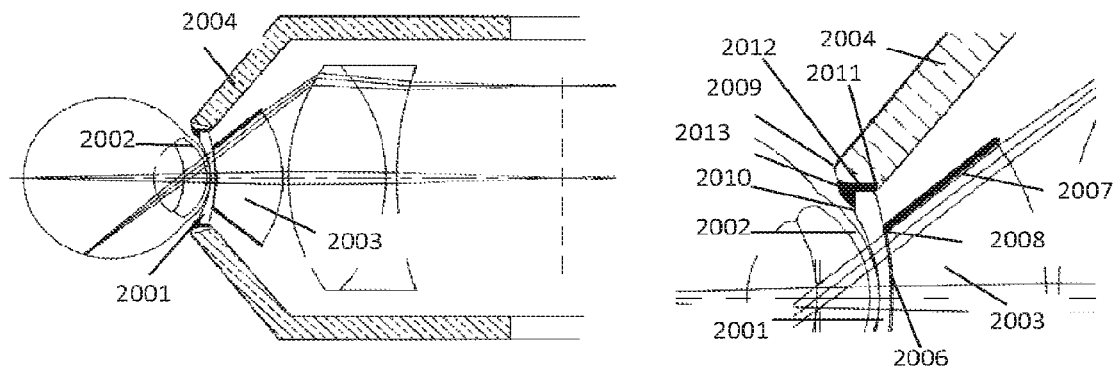
FIG. 20 schematically illustrates another embodiment of the hermetically sealed eye imaging apparatus where an adhesive is used to seal the optical window.

FIG. 20 schematically illustrates another embodiment of the imaging apparatus where an adhesive and/or a hermetically sealing material may be used to seal the optical window. The housing 2004 of the front module housing is constructed with one single piece although a multi-piece front module housing may be employed as well. The designs for the imaging lens 2003, the absorptive coating 2007, the absorptive material 2008 and the air gap 2006 are similar as the imaging lens 1903, the absorptive coating 1907, the absorptive material 1908 and the gap 1906 illustrated in FIG. 19. A small flat surface 2010 is disposed about the edge or periphery of the concave surface of the optical window 2001. An alignment edge or ring 2011 is included in the housing 2004 to help align the optical window 2001. Accordingly, the alignment ring 2011 has a vertical edge that permit lateral alignment adjustment, axial positioning, and proper orientation of the optical window in the imaging system. However, as illustrated, the housing has an opening for fitting the optical window 2001 therein and for providing a gap between the housing and optical window. As discussed above, having a larger opening and a gap 2012 permits the optical window to be laterally translated and aligned, for example, using an alignment fixture that moves the lens laterally with respect to the housing. The optical window may, for example, be properly aligned with the optical axis of the imaging lens and imaging system. The gap 2012 permits this lateral movement and alignment. Additionally, this gap 2012 provides for flow of sealing material. Accordingly, the opening in the housing is sufficiently larger such that after the optical window is centered and aligned, the gap 2012 remains disposed between the housing and the window to allow for sealing material. During manufacture, after the optical window 2001 is dropped into the housing, an elastic sealing material 2013 is applied to fill the gap between two components. The round corner 2009 at the end of the housing 2004 helps to build a smooth transition from the flat surface 2010 to the housing 2004. In various embodiments, this material comprises adhesive or epoxy, which may be elastic. In some embodiments, the sealing material 2012 comprises UV cured acrylic adhesive. In various embodiments, this sealing material may be elastic. In some such embodiments, the sealing material is not hermetic sealing material. Accordingly, in various embodiments, this seal is not a hermetic seal that can with stand the temperature of autoclaving such as temperatures greater than 120° C., 130° C., or 140° C. and less than, for example, 150° C. In other embodiments, however, the material may comprise hermetic sealing material and the seal may be a hermetic seal. The hermetically sealing material 2013 may comprise e.g., ceramic or metal.

As discussed above, in some embodiments, the hermetically sealed eye imaging apparatus comprises a hermetically sealed removable front imaging module and a main module. The hermetically sealed removable front imaging module comprises a front end and a rear end. The hermetically sealed removable front imaging module includes a first optical window, a second optical window and an imaging lens. The optical window at the front end is separated from an alignment edge of the housing with a first smaller gap configured to align the optical window using for example an alignment fixture during manufacture, and separated from a reservoir edge of the housing with a second gap larger than the first gap, configured to be a reservoir of a hermetically sealing material. The second gap is sometimes rearward the first gap, and sometimes forward the first gap. There is a first hermetical seal between this first optical window and the housing. The second optical window is exposed from a rear end of the hermetically sealed removable front imaging module. A second hermetical seal is formed between the second optical window and the rear end. The hermetically sealed removable front imaging module is capable of being repeatedly attached to and removed from the main module that includes the image sensor. The main module may further include a third optical window exposed from a front portion of the main module. In certain embodiments, the hermetically sealed eye imaging apparatus may also include a plurality of balls disposed inside and positioned against the reservoir edge of the housing. The hermetically sealed removable front imaging module may further include a first set of relay lenses configured to form a secondary image of the eye near a back focal plane of the first set of relay lenses. The main module may further include a second set of relay lenses configured to project the secondary image to infinity with a front focal plane positioned next to the back focal plane of the first set of relay lenses. The main module may further comprise a set of miniature lenses positioned near the back focal plane of the second set of relay lenses and configured to deliver light from the eye to the image sensor. The light source may be positioned within the hermetically sealed removable front imaging module, or within the main module. When the light source is within the main module, the hermetically sealed removable front imaging module and/or main module may further include a plurality of lighting coupling elements to optically couple light from the main module to the front imaging module.

The various embodiments as shown in FIG. 16, FIG. 17, FIG. 18, FIG. 19 and FIG. 20 can all use a special assembly process, where the optical window is aligned, for example, with an alignment fixture, and sealed with the housing. Other optical components including the imaging lens and the lighting fixtures may be mounted in a separated unit, and then aligned with the front optical window, which has already been aligned with the housing. The precise alignment between the optical window and the imaging lens afterward, as well as setting of the proper gap between the optical window and the imaging lens are steps that can affect the optical performance of the imaging system. The proper gap is achieved in room temperature during the assembling process with the adjustment of the position of the lens housing, which comprises the optical assembly, along the optical axis in reference to the housing of the imaging apparatus. The use of the gap between the optical surfaces of the optical window and the imaging lens helps to reduce the thermal stress and enables the application of more sophisticated hermetically sealing techniques.

Figures 21A, 21B:
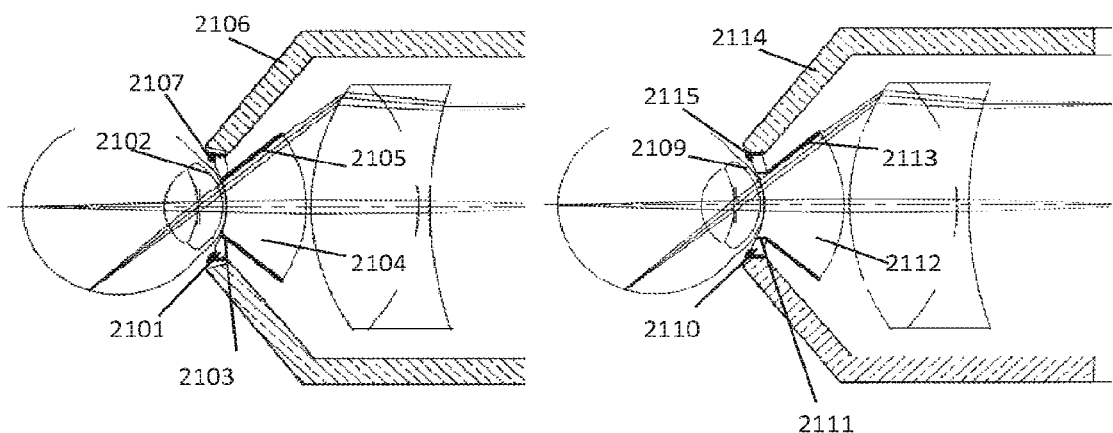
FIG. 21(A) schematically illustrates an embodiment where an opening is made in the center of the optical window to allow a portion of the imaging lens to be disposed in the opening.
FIG. 21(B) schematically illustrates another embodiment where the opening in the center of the optical window has sidewalls parallel to each other and to the optical axis of the optical imaging system thereby potentially simplifying manufacture.

In various embodiments such as shown in FIG. 21(A), an opening 2103 is disposed at the center of the optical window 2101 and a portion of the imaging lens 2104 is inserted therein. The opening may for example be drilled in the optical window 2101. Accordingly, the shape and size of the opening 2103 may be made to match that of imaging lens 2104, to allow a portion of the imaging lens 2104 to be inserted in the opening. As discussed above, the periphery of the imaging lens 2104 may be a conical shape such as a frusto-conical shape and coated with optically absorptive material 2105 whose absorption spectrum may be in the visible range to the eye and/or into invisible spectra, for example. The coating 2105 not only may prevent light from entering the imaging lens from outside, but also absorb the stray light from the eye when it enters the imaging lens 2104 along with the imaging light. The boundary formed by the absorptive coating provides higher level of separation between the illumination optical path and imaging optical path in the imaging lens 2104. The concave surface of the optical window 2101 can share the same or similar radius as the concave surface of imaging lens 2104. Both of these concave surfaces can have a curvature configured to receive the convex curvature of the cornea. In various embodiments, the optical window 2101 may be cemented with the imaging lens 2104, with their concave surface aligned for example along a common curve or reference surface thereby forming a smooth surface against the cornea of patient 2102. In various embodiments the concave surface of the optical window and the imaging lens are flush against each other. As illustrated, the imaging lens has a frusto-conical shape. The front end is smaller than the back end and thus the sidewalls are tapered. Additionally, the optical window has an inner sidewall or edge that is tapered to match the taper of the sidewalls of the imaging lens. The matching of these surface permits the imaging lens to fit in the optical window with a junction where the optical window contacts the imaging lens over the thickness of the optical window. In certain embodiments, the front optical window 2101 may comprise sapphire, optical glass or optically clear polymers.

FIG. 21(B) illustrates another embodiment with slightly modified design. As illustrated, the optical window does not have the tapered inner sidewall surfaces as shown in FIG. 21(A). Instead, the optical window 2110 has inner sidewall surfaces that are parallel to the optical axis of the imaging system and/or of the imaging lens. Such a design may be easier for manufacturing the optical window. In certain embodiments, however, the tip of the imaging lens 2112 is shaped to match that of the opening 2111 of the optical window and in particular to match the shape of the inner sidewalls of the optical window. As shown, the imaging lens is substantially frusto-conical in shape. However, the imaging lens includes a neck defined by sidewall surfaces that are straight and parallel to the central axis through the imaging lens and/or the optical axis of the imaging lens. These sidewalls are configured to match the shape of the inner sidewall surfaces of the optical window. The matching of these surface permits the imaging lens to fit in the optical window with a junction where the optical window contacts the imaging lens over the thickness of the optical window. An optical absorptive coating 2113 is applied to the edge of the imaging lens 2112, before the imaging lens 2112, is cemented with the optical window 2110. The optical window 2110 may comprise sapphire, optical glass or optically clear polymers in certain embodiments.

While the present invention has been disclosed in exemplary embodiments, those of ordinary skill in the art will recognize and appreciate that many additions, deletions and modifications to the disclosed embodiment and its variations may be implemented without departing from the scope of the invention.

What is claimed is:

1. An eye imaging apparatus comprising:
a housing;
a light source disposed inside the housing to illuminate an eye;
an optical imaging system having an optical axis and a field of view, the optical imaging system comprising:
an optical window with a concave front surface for receiving the eye; and
an imaging lens disposed behind the optical window and optically aligned with the optical window along the optical axis;
a light conditioning element in the housing positioned behind the peripheral portion of the optical window, the light conditioning element comprising:
a solid optically transmissive material in a hollow and frusto-conical shape,
a front surface,
an inner side surface disposed around a side surface of the imaging lens,
an outer side surface, wherein at least one of the inner side surface and the outer side surface comprises a multi-segment surface, and
a light channel between the inner side surface and the outer side surface with an inner edge and an outer edge at the front surface,
wherein the light conditioning element is configured to receive light from the light source and direct most of a first portion of light exiting near the inner edge to a first area of a retina of the eye that comprises approximately one-third of the field of view of the optical imaging system and which first area includes the optical axis, and most of a second portion of light exiting near the outer edge to a second area of the retina farther away from the optical axis than about two-thirds of the field of view and on an opposite side of the optical axis from the outer edge; and
an image sensor in the housing disposed to receive an image of the eye from the optical imaging system.

2. The eye imaging apparatus in claim 1, wherein the front concave surface of the optical window has a radius of curvature between 5 mm and 16 mm.

3. The eye imaging apparatus in claim 1, wherein a cross-section of the light conditioning element comprises multiple sections spaced apart by at least one barrier in a radial direction.

4. The eye imaging apparatus in claim 1, wherein the multi-segment surface comprises a substantially specularly reflective segment.

5. The eye imaging apparatus in claim 1, wherein the conditioning element is configured to direct more than 70% of the light exiting from the inner edge of the light channel to the first area.

6. The eye imaging apparatus of claim 1, wherein the light conditioning element is configured to direct more than 70% of the light exiting from the outer edge of the light channel to the second area.

7. The eye imaging apparatus in claim 1, wherein the light conditioning element is configured to direct substantially all the light exiting the light conditioning element outside an entrance pupil of the optical imaging system.

8. The eye imaging apparatus in claim 1, wherein the light conditioning element is configured such that less than 20% of light is incident on said concave front surface of the optical window within a distance of 2 mm from the optical axis of the optical imaging system.

9. The eye imaging apparatus in claim 1, wherein the multi-segment surface comprises a refractive segment.

10. The eye imaging apparatus in claim 1, wherein the multi-segment surface comprises a plurality of segments, wherein a length of each segment along the optical axis is between 0.05 mm and 2 mm.

11. The eye imaging apparatus in claim 1, wherein a number of segments in the multi-segment surface is between 2 and 20.

12. An eye imaging apparatus comprising:
a housing;
a light source disposed inside the housing to illuminate an eye;
an optical imaging system having an optical axis and a field of view, the optical imaging system comprising:

an optical window with a concave front surface for receiving the eye; and an imaging lens disposed behind the optical window and optically aligned with the optical window along the optical axis;

a light conditioning element in the housing positioned behind the peripheral portion of the optical window, the light conditioning element comprising:

a solid material in a hollow and frusto-conical shape, an inner side surface disposed around and spaced apart from a side surface of the imaging lens by a distance of less than 3.0 mm, the inner side surface comprising a multi-segment surface;

an outer side surface, and a light channel between the inner side surface and the side surface of the imaging lens, the light channel having an inner edge and an outer edge at a front end, wherein the light conditioning element is configured to receive light from the light source and direct most of a first portion of light exiting near the inner edge to a first area of a retina of the eye that comprises approximately one-third of the field of view of the optical imaging system and which first area includes the optical axis, and most of a second portion of light exiting near the outer edge to a second area of the retina farther away from the optical axis than about two-thirds of the field of view and on an opposite side of the optical axis from the outer edge; and an image sensor in the housing disposed to receive an image of the eye from the optical imaging system.

13. The eye imaging apparatus in claim 12, wherein a cross-section of the light conditioning element comprises multiple sections spaced apart by at least one barrier in a radial direction.

14. The eye imaging apparatus in claim 12, wherein the multi-segment surface comprises a plurality of segments, wherein a length of each segment along the optical axis is between 0.05 mm and 2 mm.

15. An eye imaging apparatus comprising:

a housing;

a light source disposed inside the housing to illuminate an eye;

an optical imaging system having an optical axis and a field of view, the optical imaging system comprising:

an optical window with a concave front surface for receiving the eye; and an imaging lens disposed behind the optical window and optically aligned with the optical window along the optical axis;

a light conditioning element in the housing positioned behind the peripheral portion of the optical window, the light conditioning element comprising:

a solid optically transmissive material in a hollow and frusto-conical shape, an inner side surface disposed around and spaced apart from a side surface of the imaging lens by a distance of less than 3.0 mm, the inner side surface comprising a multi-segment surface;

an outer side surface, a first light channel between the inner side surface and the side surface of the imaging lens, the first light channel having an inner edge at a front end of the side surface, a second light channel between the inner side surface and the outer side surface, the second light channel having an outer edge at a front end of the outer side surface, wherein the light conditioning element is configured to receive light from the light source and direct most of a first portion of light exiting near the inner edge to a first area of a retina of the eye that comprises approximately one-third of the field of view of the optical imaging system and which first area includes the optical axis, and most of a second portion of light exiting near the outer edge to a second area of the retina farther away from the optical axis than about two-thirds of the field of view and on an opposite side of the optical axis from the outer edge; and an image sensor in the housing disposed to receive an image of the eye from the optical imaging system.

16. The eye imaging apparatus in claim 15, wherein a cross-section of the light conditioning element comprises multiple sections spaced apart by at least one barrier in a radial direction.

17. The eye imaging apparatus in claim 15, wherein the multi-segment surface comprises a plurality of segments, wherein a length of each segment along the optical axis is between 0.05 mm and 2 mm.

18. The eye imaging apparatus in claim 15, wherein the multi-segment surface comprises a refractive segment.

* * * * *